United States Patent [19]

Mookherjee et al.

[11] 4,391,717

[45] Jul. 5, 1983

[54] USE OF ISOMERIC FARNESENE PRODUCT-BY-PROCESS FOR AUGMENTING OR ENHANCING THE AROMA OF PERFUME COMPOSITIONS, COLOGNES AND PERFUMED ARTICLES

[75] Inventors: Braja D. Mookherjee, Holmdel; Robert W. Trenkle, Bricktown, both of N.J.; Bernard J. Chant, Rye, N.Y.; Anton V. Ouwerkerk, Livingston, N.J.; Venkatesh Kamath, Red Bank, N.J.; Cynthia J. Mussinan, Bricktown, N.J.

[73] Assignee: International Flavors & Fragrances Inc., New York, N.Y.

[21] Appl. No.: 375,534

[22] Filed: May 6, 1982

Related U.S. Application Data

[62] Division of Ser. No. 292,392, Aug. 13, 1981.

[51] Int. Cl.$^3$ .................................................. D06M 13/16
[52] U.S. Cl. .................................... 252/8.6; 428/905
[58] Field of Search ........................................ 252/8.6

[56] References Cited

U.S. PATENT DOCUMENTS

| | | | |
|---|---|---|---|
| 3,505,432 | 4/1970 | Neuwald | 264/4 |
| 3,553,296 | 1/1971 | Gaeckel | 252/522 A |
| 3,632,396 | 1/1972 | Perez-Zamora | 428/294 |
| 4,247,498 | 1/1981 | Castro | 264/41 |

*Primary Examiner*—Maria Parrish Tungol
*Attorney, Agent, or Firm*—Arthur L. Liberman

[57] ABSTRACT

Described are isomeric mixtures of farnesene prepared by dehydrating nerolidol using potassium bisulfate or paratoluene sulfonic acid and then distilling the resultant product at particular temperature ranges and particular pressure ranges in order to prepare a composition of matter useful for augmenting or enhancing waxy, white-flowery (magnolia-like, tuberose, gardenia-like) aromas with citrusy (lemon/lime), pettit-grain-like undertones and green top notes in perfume compositions, colognes and perfumed articles (e.g., solid or liquid anionic, cationic, nonionic or zwitterionic detergents, fabric softener compositions, dryer-added fabric softener articles, cosmetic powders and the like).

3 Claims, 32 Drawing Figures

GLC PROFILE FOR EXAMPLE I.

GLC PROFILE FOR EXAMPLE I.

IR SPECTRUM FOR EXAMPLE I, BULKED FRACTIONS 4-18.

IR SPECTRUM FOR PEAK II OF FIG. 2 OF EXAMPLE I.

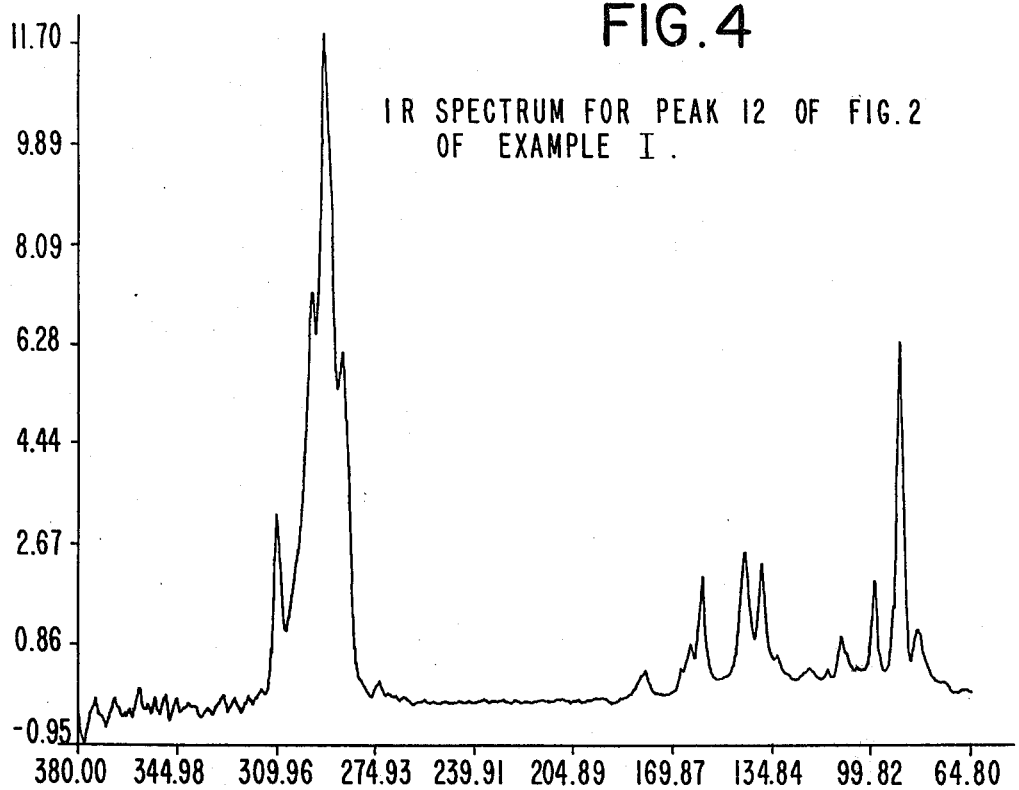
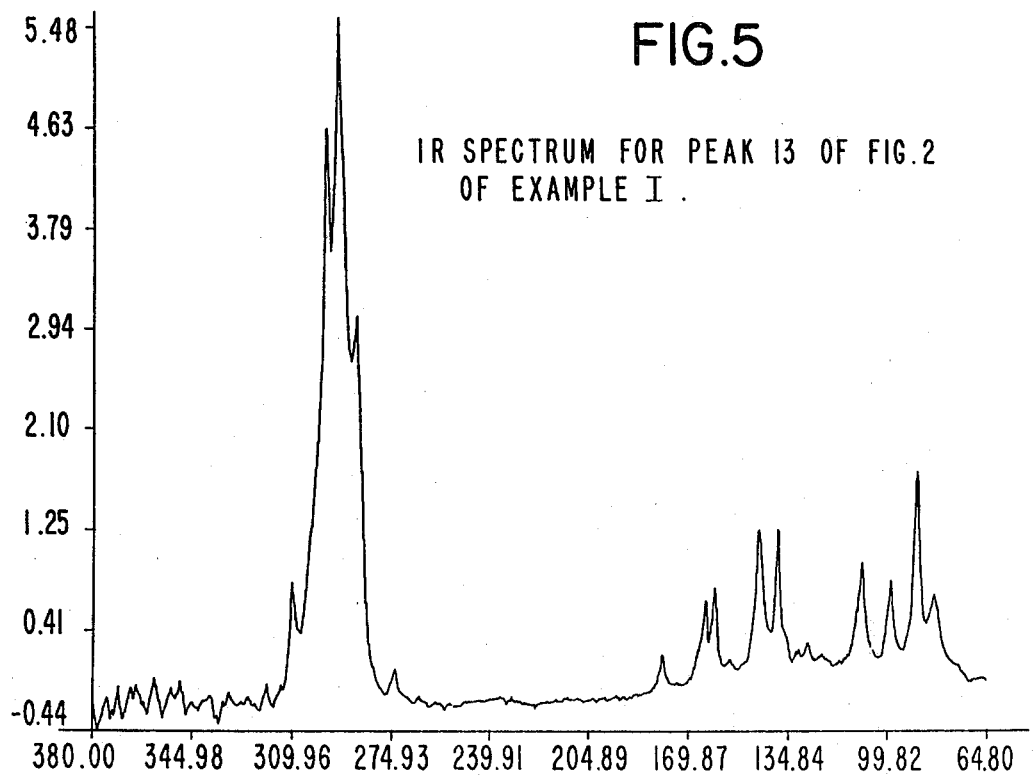

IR SPECTRUM FOR PEAK 14 OF FIG. 2 OF EXAMPLE I.

NMR SPECTRUM FOR PEAK 11 OF FIG. 2 OF EXAMPLE I.

NMR SPECTRUM FOR PEAK 12 OF FIG.2 OF EXAMPLE I.

NMR SPECTRUM FOR PEAK 13 OF FIG.2 OF EXAMPLE I

NMR SPECTRUM FOR PEAK 14 OF FIG.2 OF EXAMPLE I.

GLC PROFILE FOR EXAMPLE II.

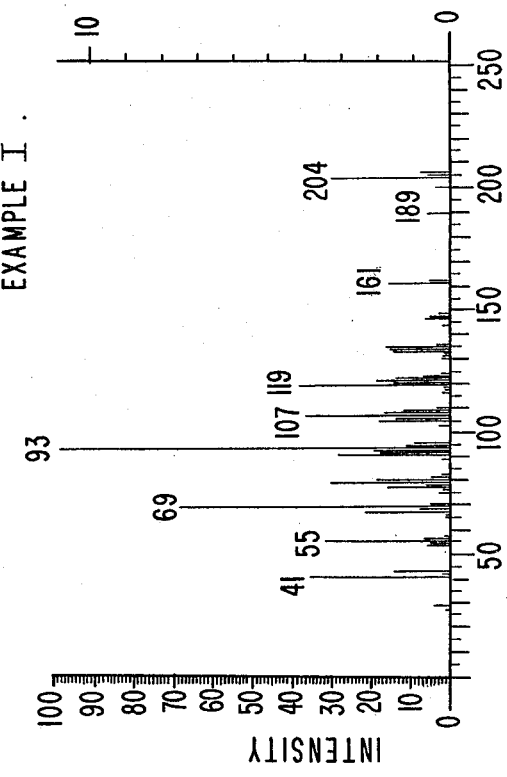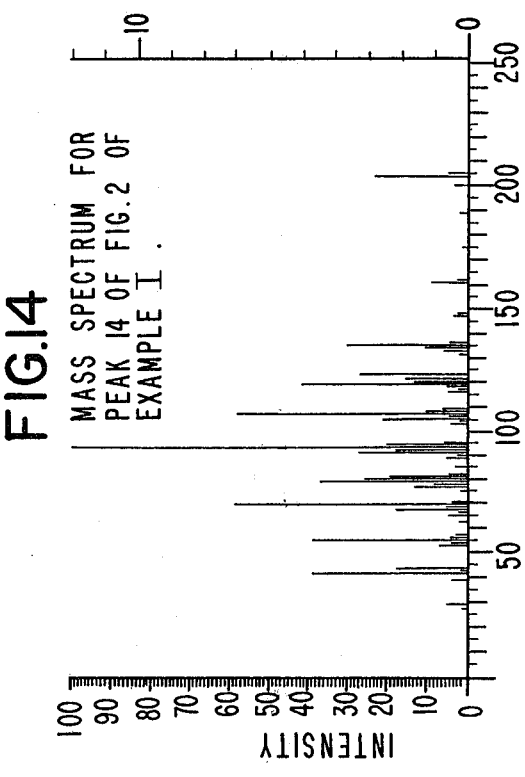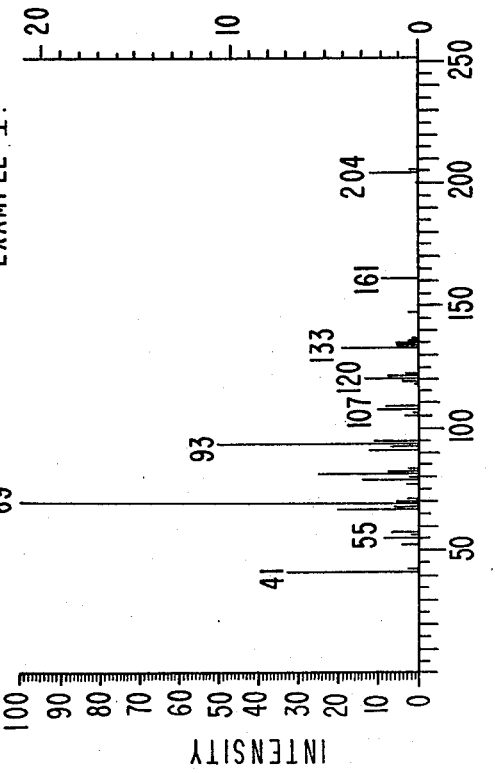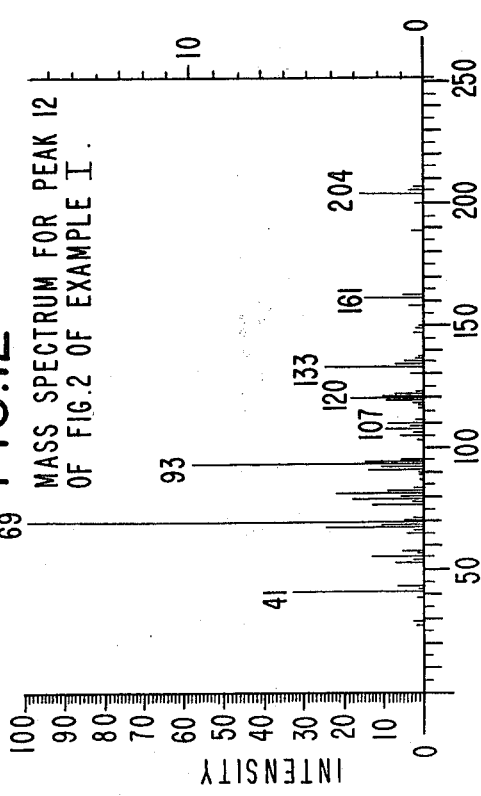

GLC PROFILE FOR EXAMPLE III _ CRUDE.

GLC PROFILE FOR FRACTION 1 OF EXAMPLE III.

GLC PROFILE FOR FRACTION 2 OF EXAMPLE III.

GLC PROFILE FOR FRACTION 3 OF EXAMPLE III.

GLC PROFILE FOR FRACTION 4 OF EXAMPLE III.

GLC PROFILE FOR FRACTION 5 OF EXAMPLE III.

GLC PROFILE FOR FRACTION 6 OF EXAMPLE III.

GLC PROFILE FOR FRACTION 7 OF EXAMPLE III.

GLC PROFILE FOR FRACTION 8 OF EXAMPLE III.

GLC PROFILE FOR FRACTION 9 OF EXAMPLE III.

GLC PROFILE FOR BULKED FRACTIONS 4-7 OF EXAMPLE III.

IR SPECTRUM FOR BULKED FRACTIONS 4-7 OF EXAMPLE III.

GLC PROFILE FOR EXAMPLE IV. (BULKED FRACTIONS 4-8)

GLC PROFILE FOR EXAMPLE IV. (CRUDE REACTION PRODUCT)

GLC PROFILE FOR EXAMPLE I (NEROLIDOL REACTANT)
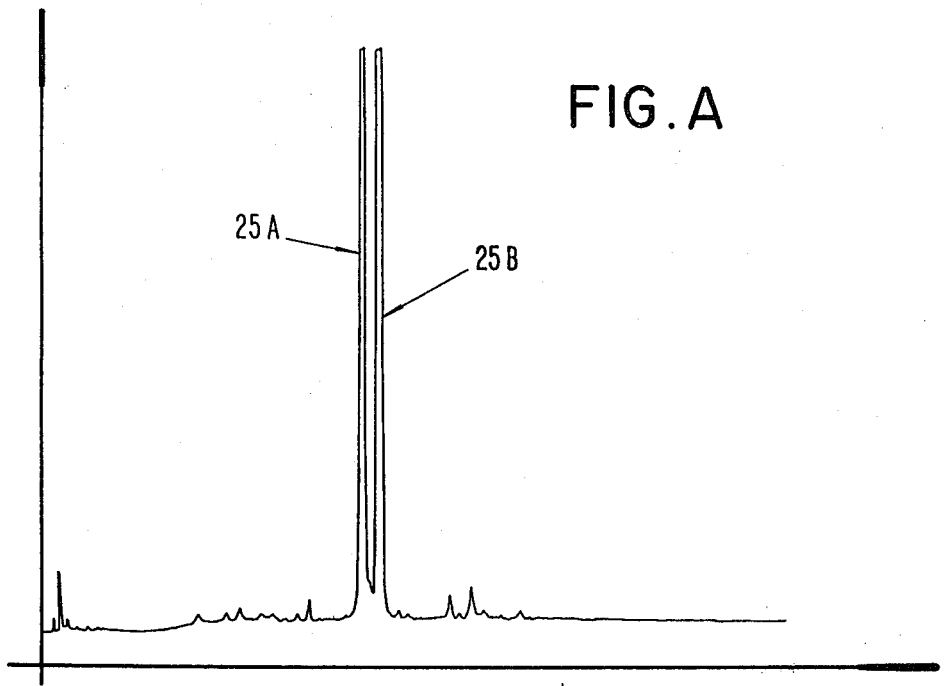
FIG. A
GLC PROFILE FOR EXAMPLE III (NEROLIDOL REACTANT)
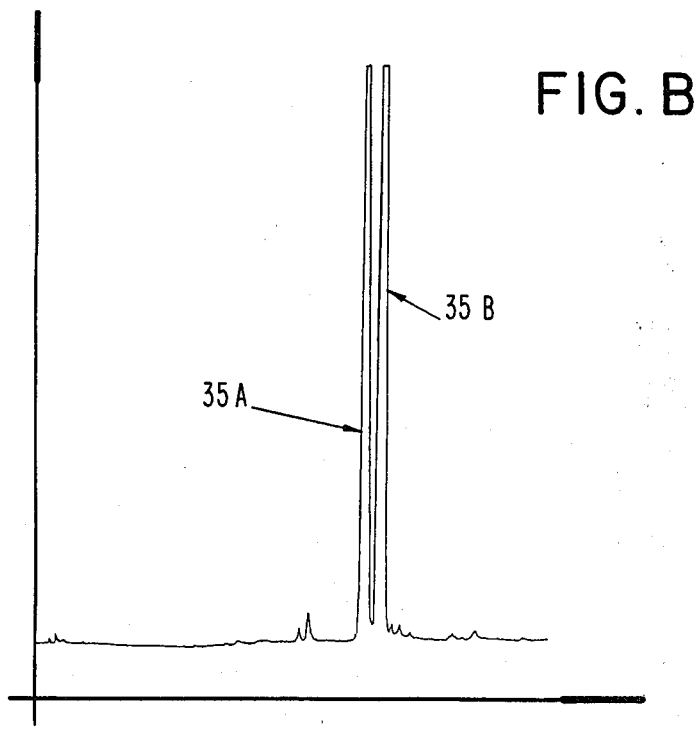
FIG. B

USE OF ISOMERIC FARNESENE PRODUCT-BY-PROCESS FOR AUGMENTING OR ENHANCING THE AROMA OF PERFUME COMPOSITIONS, COLOGNES AND PERFUMED ARTICLES

This is a divisional of application Ser. No. 292,392, filed Aug. 13, 1981.

BACKGROUND OF THE INVENTION

The present invention relates to farnesene isomer mixtures containing, but not limited to, compounds defined according to the structures:

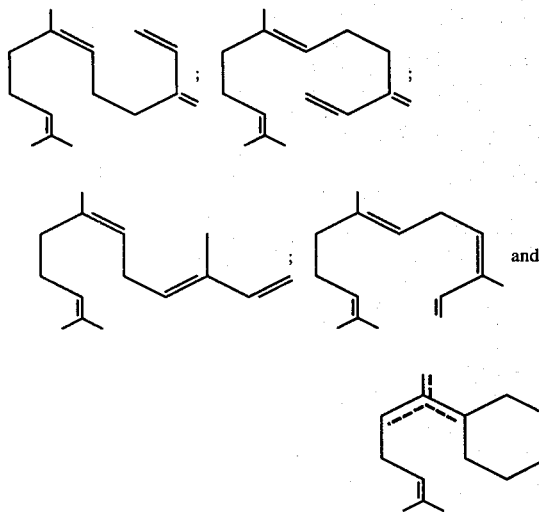

and uses of such mixtures in augmenting or enhancing the aroma of perfume compositions, perfumed articles and colognes. The compositions of our invention are prepared by dehydrating using potassium bisulfate or paratoluene sulfonic acid dehydrating agents, nerolidol compositions of matter containing the nerolidol isomers:

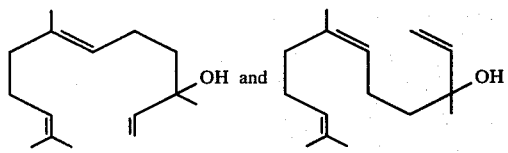

There has been considerable work performed relating to substances which can be used to impart (modify, augment or enhance) fragrances to (or in) various consumable materials. The substances are used to diminish the use of natural materials, some of which may be in short supply and to provide more uniform properties in the finished product.

Waxy, white-flowery (magnolia-like, tuberose and gardenia-like) aromas which are very close to the corresponding natural magnolia-like, tuberose and gardenia-like aromas, with citrusy (lemon/lime), pettitgrain-like undertones and green top notes are particularly desirable in several types of perfume compositions, perfumed articles and colognes.

Such aromas with the floral wet petal "morning dew" aromas are even more interesting in the field of perfumery.

Arctander "Perfume and Flavor Chemicals (Aroma Chemicals)" at monograph 1378 discloses "Farnesal", 2,6,10-trimethyl-2,6,10-dodecatrien-12-al to have a very mild, sweet oily, slightly woody, tenacious odor. On the other hand, Arctander also describes, at Monograph 1379, Farnesene, 2,6,10-trimethyl-2,6,9,11-dodecatetraene defined according to the structure:

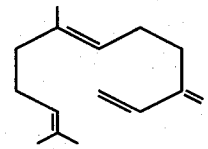

to have a very mild, sweet and warm, rather nondescript odor of good tenacity. Arctander further states that apart from some possible use in the reconstruction of certain essential oils, there is to the author's knowledge, very little, if any, use for this sesquiterpene in perfumery as such. Arctander further states that Farnesene having the structure:

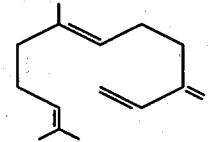

is produced by dehydration of Farnesol by heat with a potassium dehydrating agent or from Nerolidol by heat with acetic anhydride.

Brieger, et al, J. Org. Chem. Volume 34, Number 12, December 1969, in their paper "The Synthesis of trans,-trans-α-Farnesene" discloses dehydration of nerolidol using bisulfate at 170° C. to yield a number of Farnesene isomers according to the reaction:

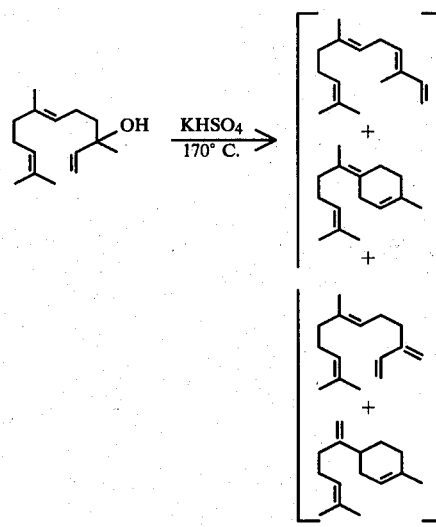

Brieger, et al also discloses the dehydration of Farnesol using potassium bisulfate at 170° C. as follows:

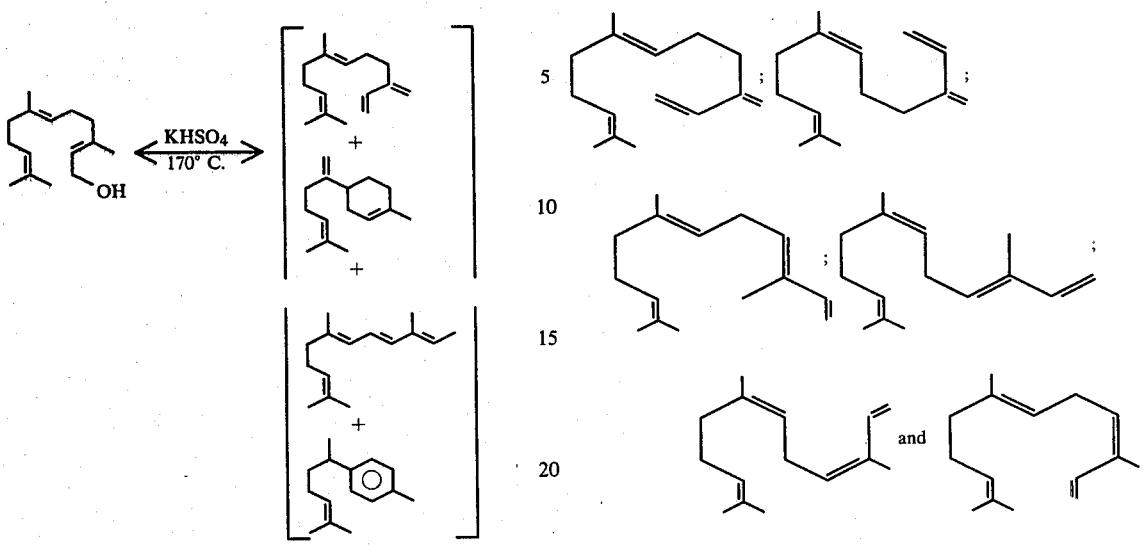

Brieger also teaches the dehydration of Farnesol using potassium hydroxide at 210° C. to yield certain isomers according to the following reaction:

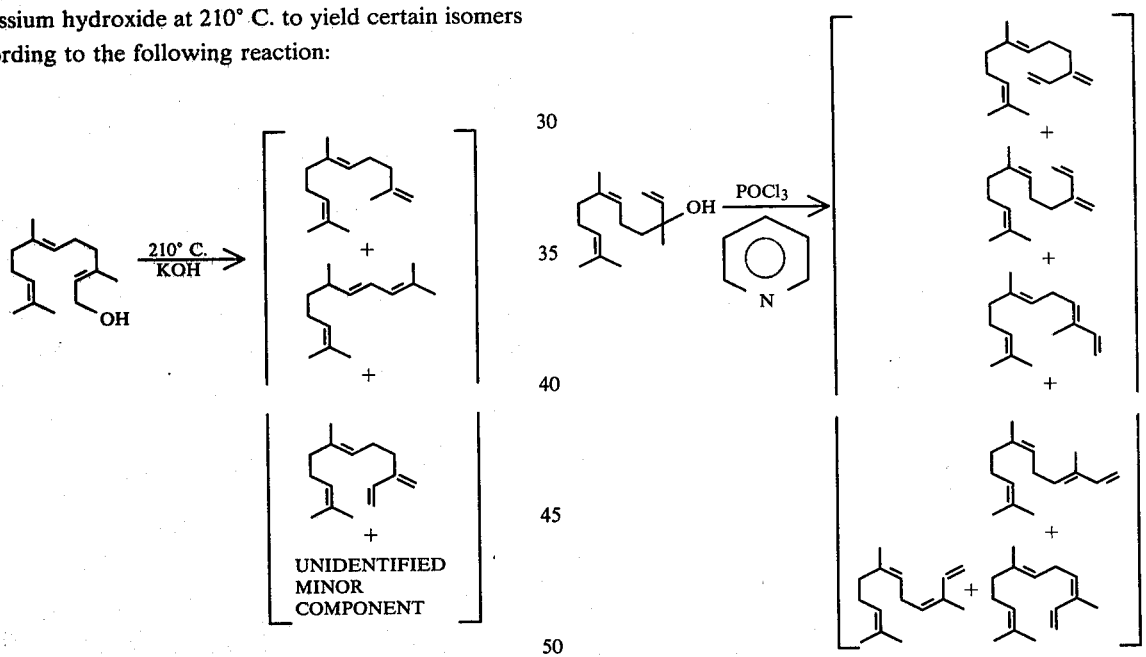

Anet, Aust. J. Chem., 1970, 23, 2101-8, in a paper entitled "Synethesis of (E,Z)-α-,(Z,Z)-α-, and (Z)-β-Farnesene" discloses the dehydration of (E)-nerolidol having the structure:

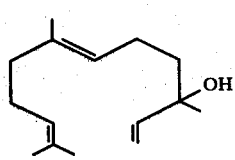

in the presence of such dehydrating agents as phosphoryl chloride in pyridene to yield the compounds having the structures:

according to the reaction:

In a paper by Hattori, et al entitled "Chemical Composition of the Absolute from Gardenia Flower" and in another paper by Tsuneya, et al entitled "GC-MS Analysis of Gardenia Flower Volatiles", it is disclosed that α-farnesene is existent in gardenia flower absolute. The Hattori, et al and Tsuneya, et al papers are published in the "VII International Congress of Essential Oils; Japan Flavor and Fragrance Manufacturers' Association", Tokyo (1979) at pages 451 and 454, respectively (papers 128 and 129, respectively).

Nothing in the prior art cited above indicates the subject matter of our invention.

BRIEF DESCRIPTION OF THE DRAWINGS

FIG. A is the GLC profile for the nerolidol used as a reactant in Example I.

FIG. B is the GLC profile for the nerolidol used as a reactant in Example III.

FIG. 4 is the infra-red spectrum for peak 12 of the GLC profile of FIG. 2.

FIG. 5 is the infra-red spectrum of peak 13 of the GLC profile of FIG. 2.

FIG. 11 is the mass spectrum for peak 11 of the GLC profile of FIG. 2.

FIG. 12 is the mass spectrum for peak 12 of the GLC profile of FIG. 2.

FIG. 13 is the mass spectrum for peak 13 of the GLC profile of FIG. 2.

FIG. 14 is the mass spectrum for peak 14 of the GLC profile of FIG. 2.

DETAILED DESCRIPTION OF THE DRAWINGS

A. DETAILED DESCRIPTION OF FIG. A

Figure 1:
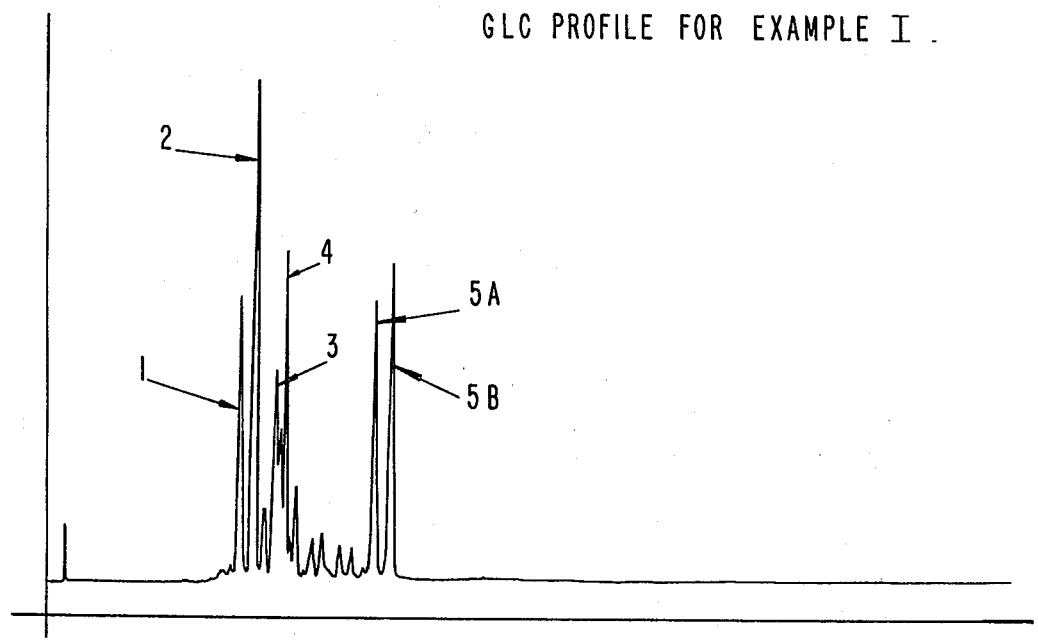
FIG. 1 is the GLC profile subsequent to basic wash but prior to distillation for the reaction product of Example I.

FIG. A is the GLC profile for the nerolidol reactant used for Example I. Reference numeral 25A and reference numeral 25B indicate the nerolidol reactant peaks for the compounds having the structures:

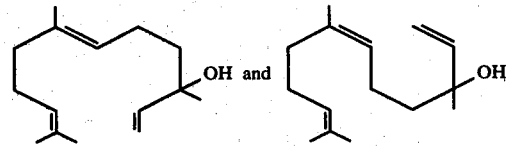

The GLC conditions are: 5% Carbowax 10'×⅛" column programmed at 100°-230° C. at 4° C. per minute.

FIG. B is the GLC profile for the nerolidol reactant used in Example III. Reference numeral 35A and 35B indicate the peaks for the nerolidol reactant on this GLC profile. The nerolidol reactants have the structures:

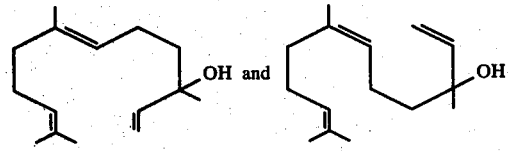

The GLC conditions are: 10'×⅛" 5% Carbowax column programmed at 100°-230° C. at 4° C. per minute.

FIG. 1 is the GLC profile for the reaction product of Example I subsequent to the base wash but prior to distillation. The GLC conditions are: 10'×⅛" 5% Carbowax column programmed at 100°-220° C. at 4° C. per minute. The peak indicated by reference numeral 1 indicates the compound having the structure:

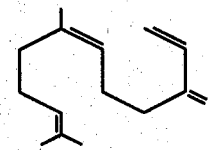

The peak indicated by reference numeral 2 is for the compound having the structure:

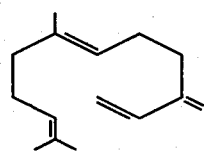

The peak indicated by reference numeral 3 is for the compound having the structure:

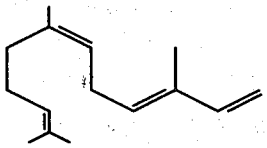

The peak indicated by reference numeral 4 is for the compounds having the structures:

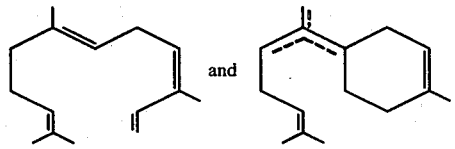

wherein the structure:

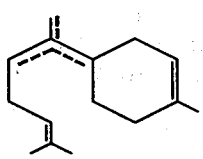

represents a mixture of compounds wherein in each of the molecules of the mixture, one of the dashed lines represents a pi double bond and each of the other of the dashed lines are indicative of single bonds. The peaks indicated by reference numerals 5A and 5B are isomers of nerolidol, the starting material, said nerolidol having the structures:

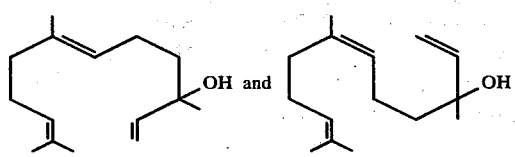

Figure 2:
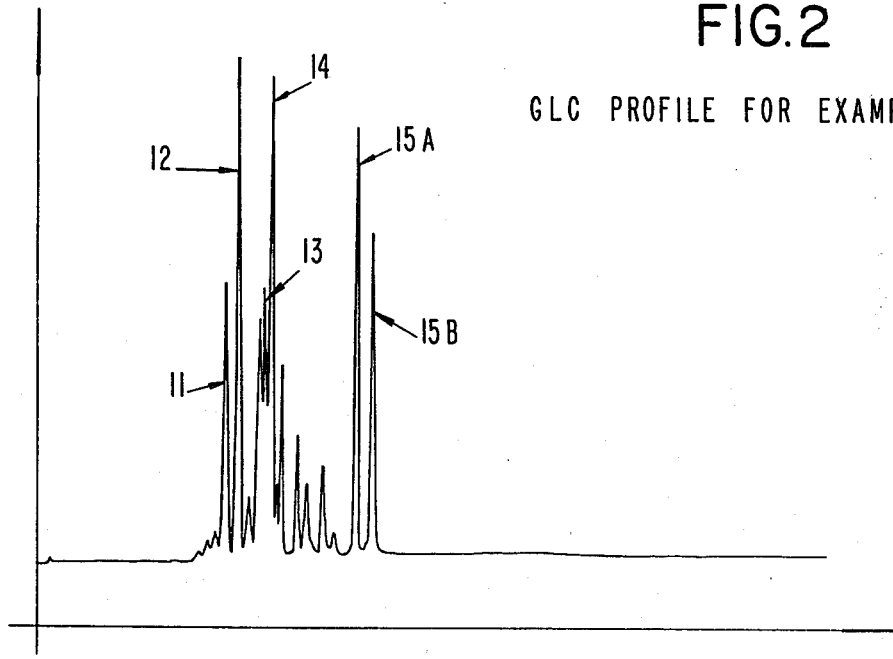
FIG. 2 is the GLC profile for bulked fractions 4-18 of the distillation product of the reaction product of Example I.
Figure 2A:
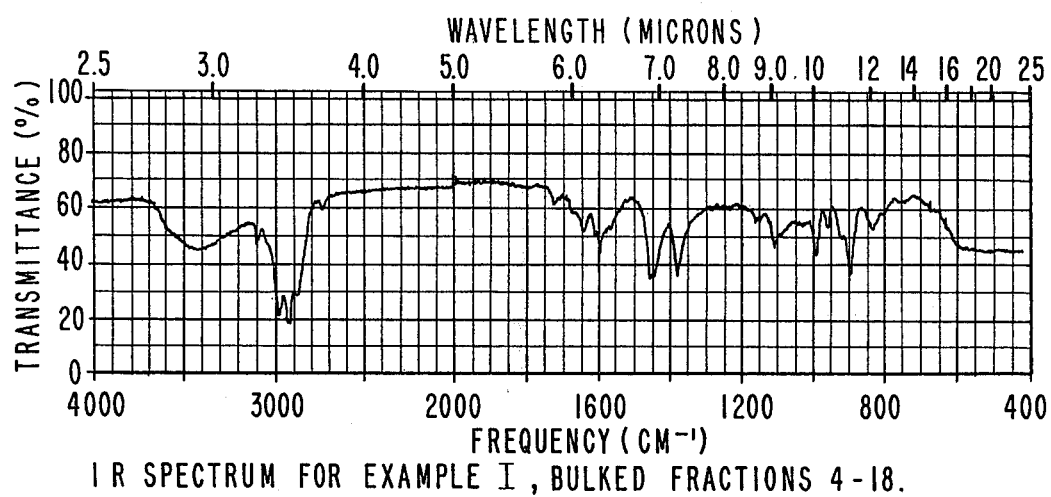
FIG. 2(A) is the infra-red spectrum for bulked fractions 4-18 of the distillation product of the reaction product of Example I.
Figure 3:
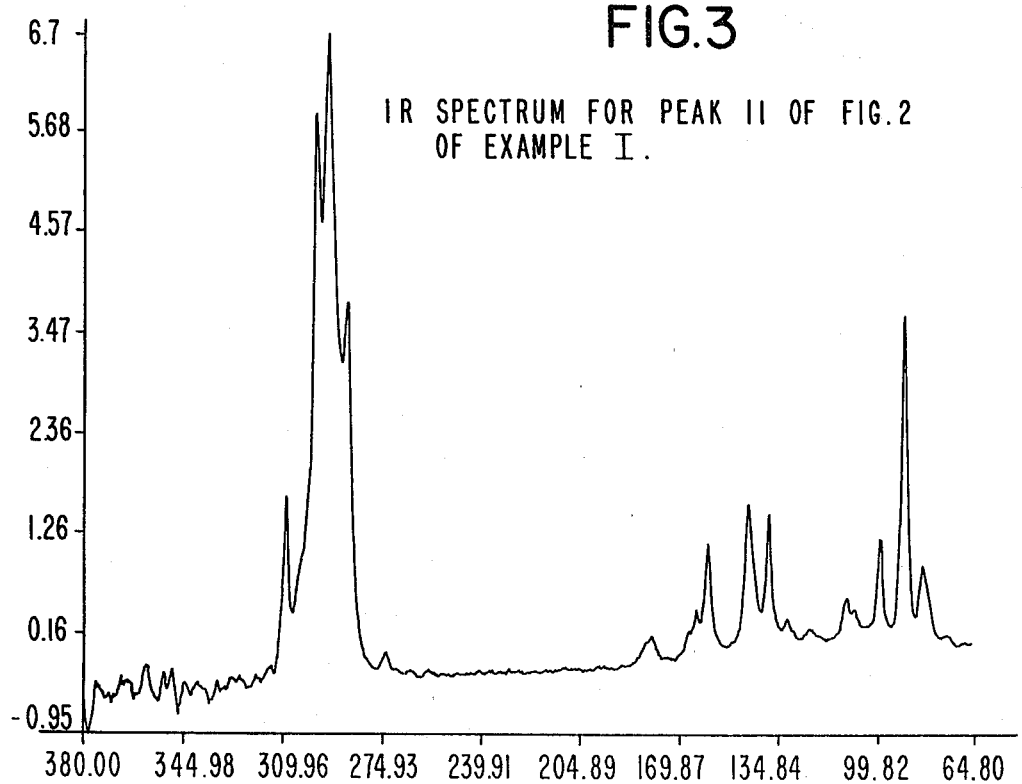
FIG. 3 is the infra-red spectrum for peak 11 of the GLC profile of FIG. 2.
Figure 6:
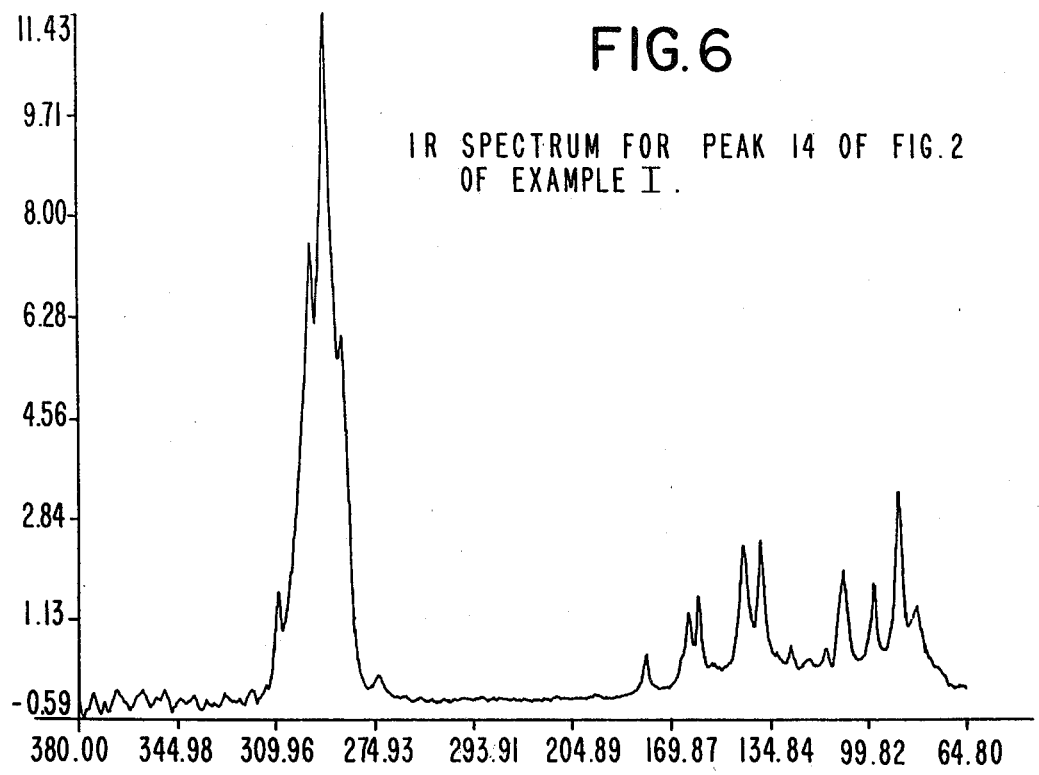
FIG. 6 is the infra-red spectrum for peak 14 of the GLC profile of FIG. 2.
Figure 7:
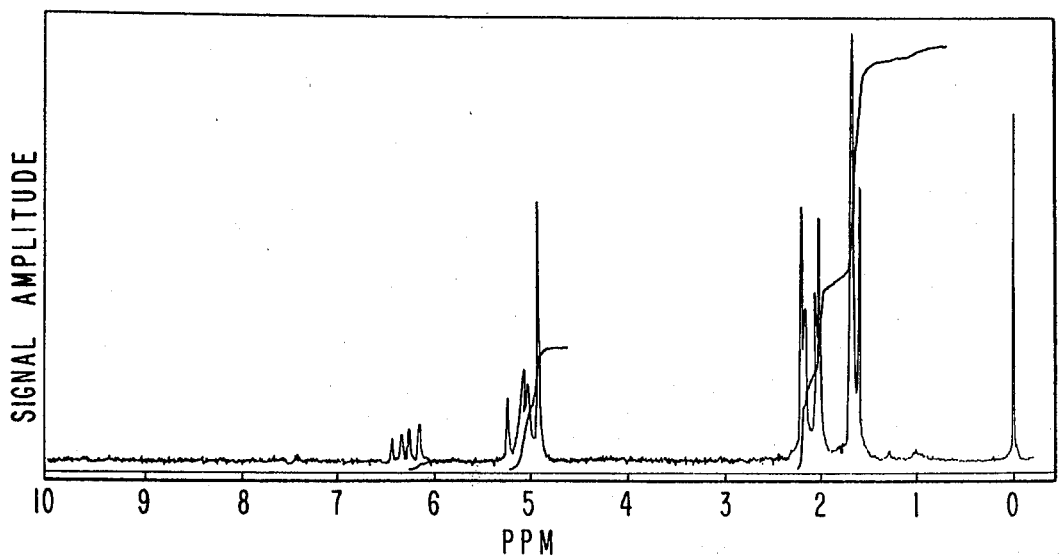
FIG. 7 is the NMR spectrum for peak 11 of the GLC profile of FIG. 2.
Figure 8:
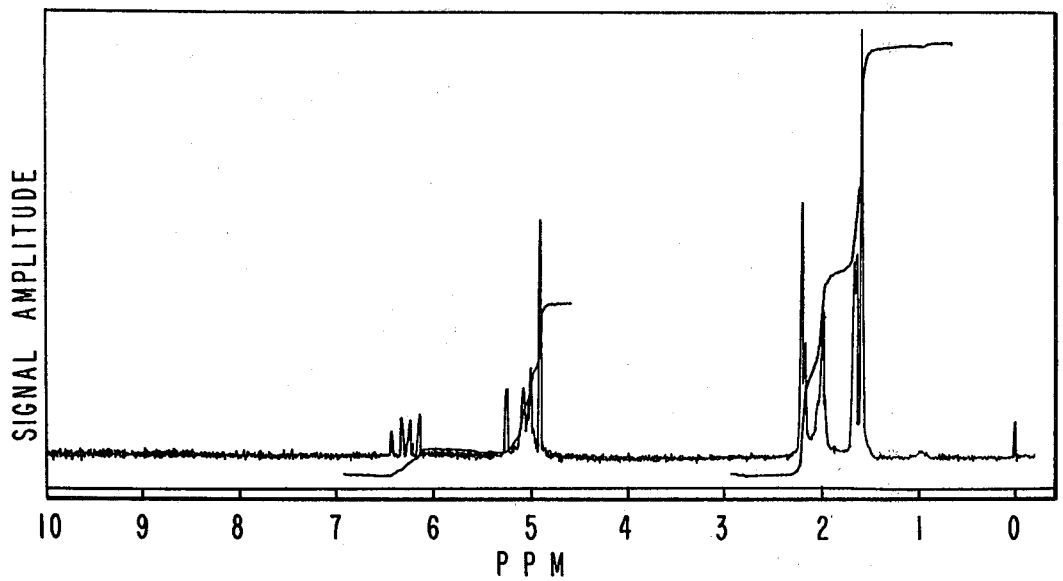
FIG. 8 is the NMR spectrum for peak 12 of the GLC profile of FIG. 2.
Figure 9:
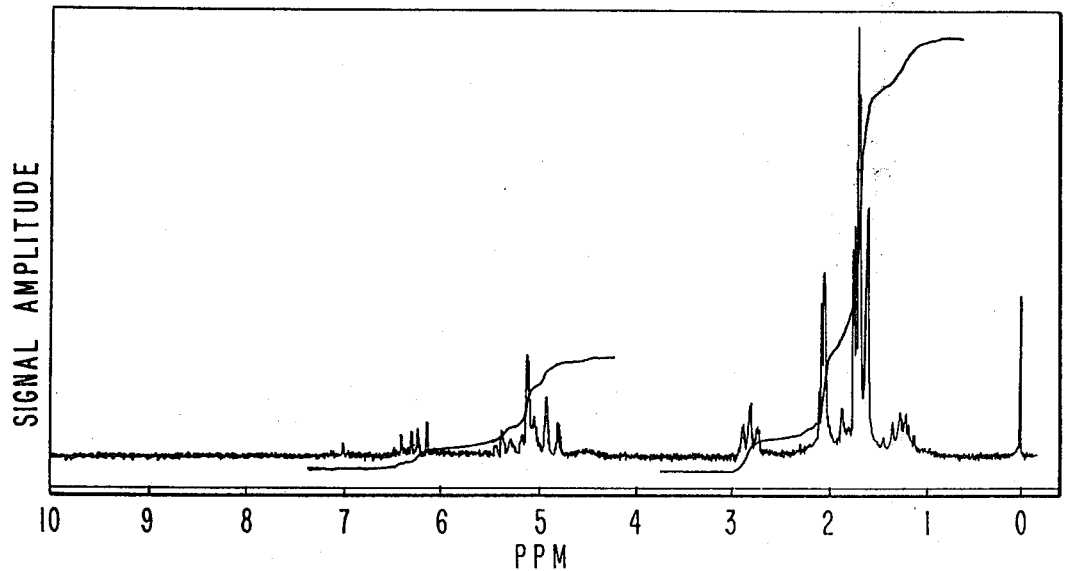
FIG. 9 is the NMR spectrum for peak 13 of the GLC profile of FIG. 2.
Figure 10:
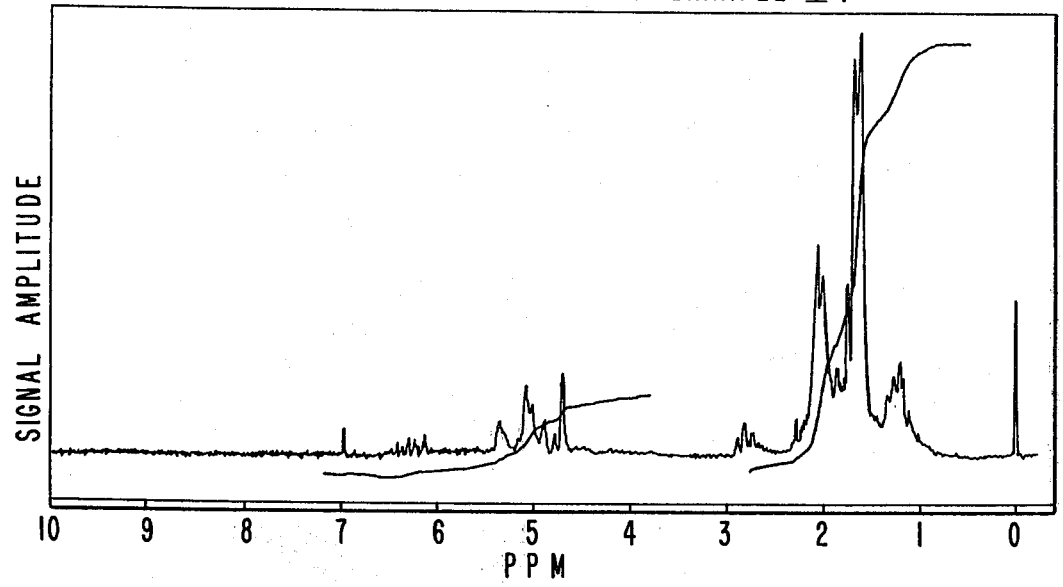
FIG. 10 is the NMR spectrum for peak 14 of the GLC profile of FIG. 2.

FIG. 2 is the GLC profile for bulked fractions 4–18 of the distillation product of the reaction product of Example I containing isomers of farnesene and isomers of nerolidol. Conditions: 10'×⅛" 5% Carbowax column programmed at 100°–220° C. at 4° C. per minute. The peak indicated by reference numeral 11 is for the compound having the structure:

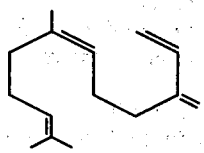

The peak indicated by reference numeral 12 is for the compound having the structure:

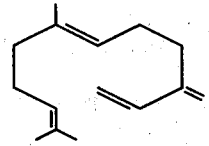

The peak indicated by reference numeral 13 is for the compound having the structure:

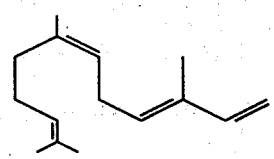

The peak indicated by reference numeral 14 is for the compounds defined according to the structures:

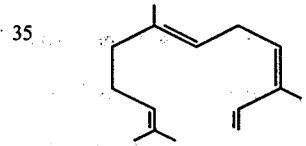

wherein the structure:

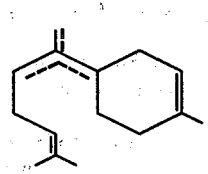

is indicative of a mixture wherein in each of the molecules of the mixture, one of the dashed lines represents a pi double bond and each of the other of the dashed lines is indicative of a single bond. The peaks indicated by reference numeral 15A and 15B are for isomers of nerolidol having the structures:

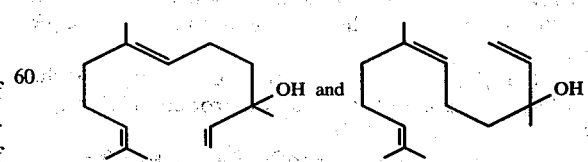

Figure 15:
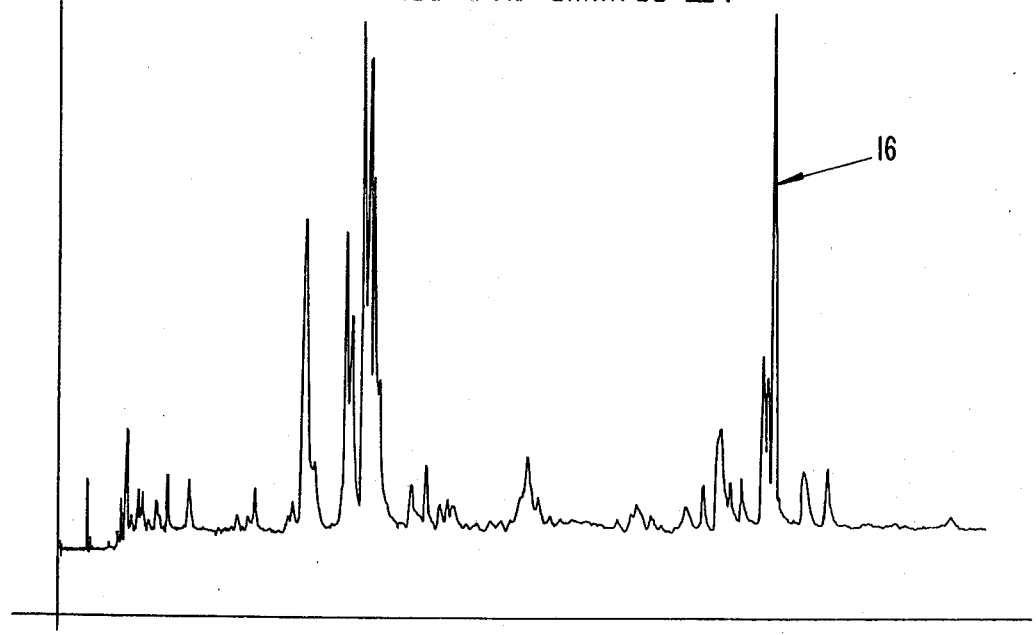
FIG. 15 is the GLC profile for the magnolia headspace of Example II.

FIG. 15 is the GLC profile for the magnolia headspace produced according to Example II. The peak indicated by reference 16 is for α-farnesene which contains compounds having the structures:

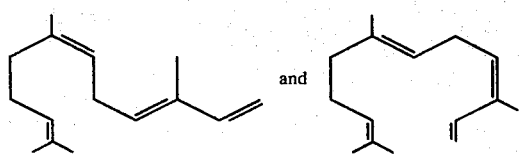

among other compounds. The conditions for this GLC profile are: SF 96 column, isothermal, 190° C.

Figure 18:
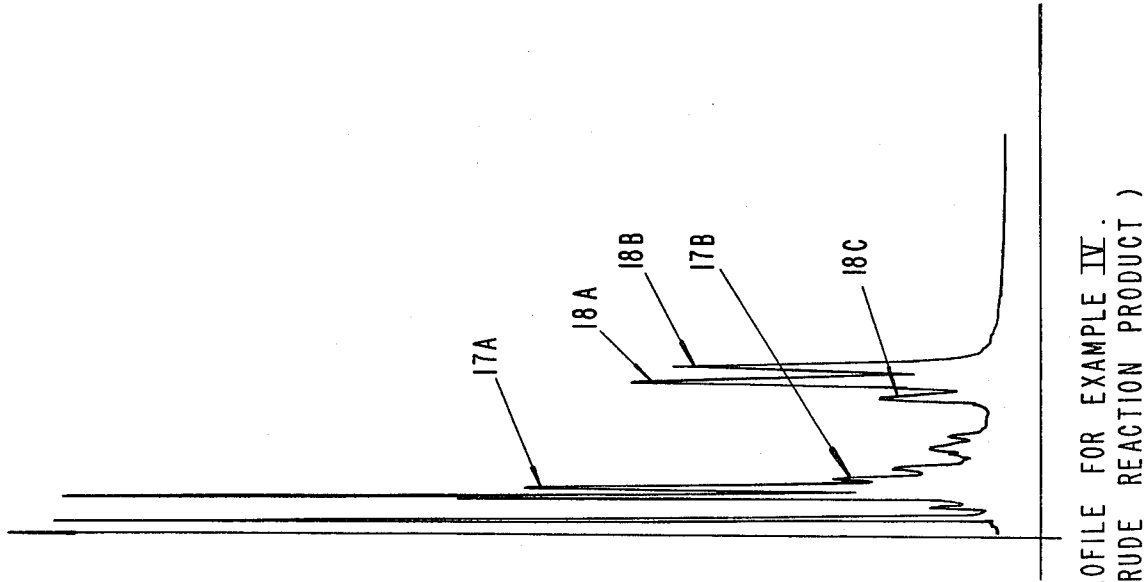
FIG. 18 is the GLC profile for the crude reaction product of Example IV.

FIG. 18 is the GLC profile for the crude reaction product of Example IV. The conditions for this GLC profile are: 10'×⅛" 5% Carbowax column programmed at 220° C. isothermal. The peaks indicated by reference numerals 17A and 17B are for various farnesene isomers containing, interalia, the compound having the structure:

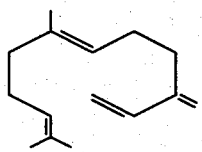

The peaks indicated by reference numerals 18A, 18B and 18C are for farnesyl acetate isomers having the structures:

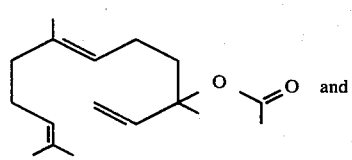

and

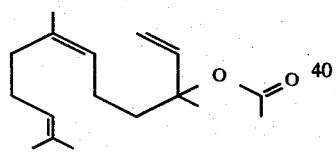

Figure 19:
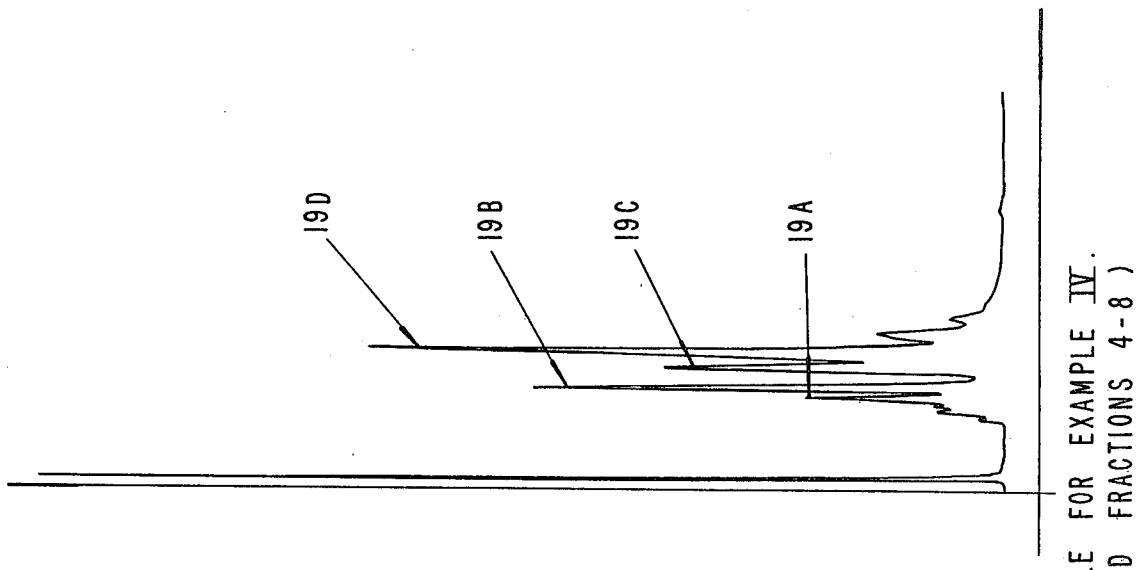
FIG. 19 is the GLC profile for bulked fractions 4-8 of the distillation product of the reaction product of Example IV.

FIG. 19 is the GLC profile for bulked fractions 4–8 of the distillation product of the reaction product of Example IV. The conditions for this GLC profile are: 10'×⅛" 5% Carbowax column programmed at 200° C. isothermal. The peaks indicated by reference numeral 19A, 19B, 19C and 19D are for farnesene isomers containing the compound having the structure:

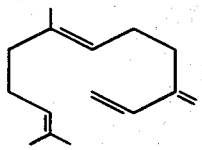

as well as other compounds.

THE INVENTION

It has now been discovered that novel solid and liquid perfume compositions, colognes and perfumed articles having very natural, waxy, flowery, wet petal (reminiscent of magnolia, tuberose and gardenia) aromas with citrusy (lemon/lime), petitgrain-like undertones and green top notes may be provided by an isomeric mixture of farnesene derivatives (containing a number of other compounds) defined according the process for producing same by the dehydration of various isomeric mixtures of E(trans) and Z(cis) nerolidol having the structures:

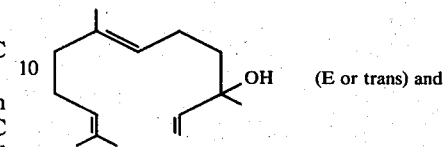

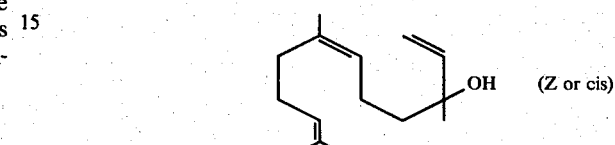

using a potassium acid sulfate or paratoluene sulfonic acid dehydration catalyst over a particular temperature and pressure range for a given reaction time range.

The reaction to produce the products of our invention may be set forth as follows:

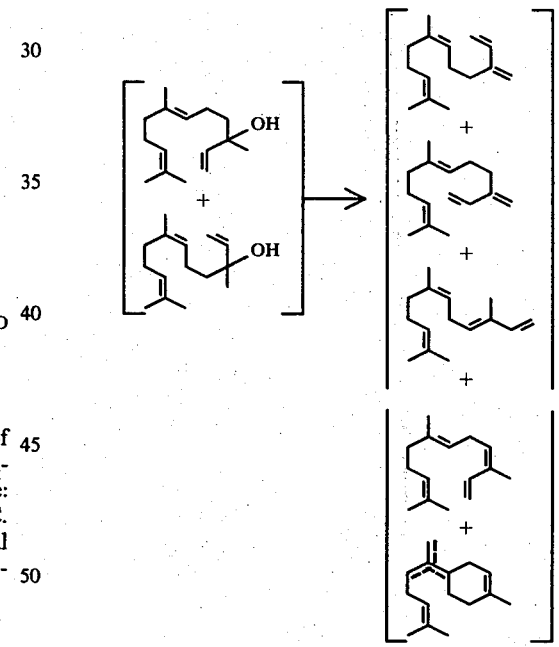

wherein the catalyst used may be potassium acid sulfate (KHSO₄) or paratoluene sulfonic acid.

The ratio of E(trans) or Z(cis) nerolidol isomers having the structures:

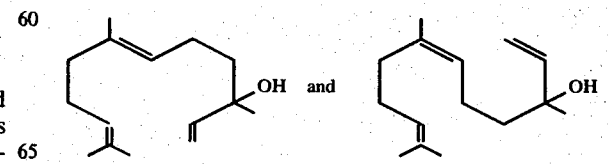

used in the reaction mass may vary from 25:100 E isomer:Z isomer up to 100:25 E isomer:Z isomer. Although the isomer mixture is substantially the same whether using the paratoluene sulfonic acid catalyst or the potassium acid sulfate catalyst, the specific reaction conditions using the two catalysts are different.

Thus, when using a potassium acid sulfate catalyst, the temperature range is preferably between 180° and 200° C. and it is necessary to utilize a solvent for the reaction mass which will:

(a) be inert to the reaction;
(b) have a boiling point at the reaction pressure which will be conveniently greater than the reaction temperature so that the solvent will not volatilize from the reaction mass.

Thus, when using a potassium acid sulfate catalyst at a temperature in the range of 180°-200° C., it is most preferable to use a heavy hydrocarbon mineral oil, for example, Primol ® (manufactured by the Exxon Corporation of Linden, N.J.). Other inert solvents such as toluene and xylene may be used but, when using toluene, the pressure over the reaction mass must be such that the reaction mass will reflux in the range of 180°-200° C. Thus, when using a toluene or xylene solvent, a positive nitrogen pressure over the reaction mass is necessary in order to maintain the reaction temperature at 180°-200° C. Thus, when using a potassium acid sulfate catalyst, not only is the temperature range important, e.g. 180°-200° C., but the pressure range is equally as important; from 1 up to 200 atmospheres pressure. Using pressures greater than 1 atmosphere necessitates the use of high pressure equipment and appropriate safety proportions.

Whether using a potassium acid sulfate catalyst or a paratoluene sulfonic acid catalyst, it is necessary to remove the water of reaction as it is formed. Thus, during refluxing, a phase separation column is necessarily utilized whereby the water of reaction is removed during the course of the reaction. For example, a Bidwell water trap is the type of trap used in the laboratory when removing the water of reaction.

Accordingly, the time of reaction is necessarily dictated by the rate at which the nerolidol reaction mixture is added to the catalyst/solvent mixture. It is preferable to add the nerolidol to the catalyst/solvent mixture over a period of between 5 and 20 hours.

When using a paratoluene sulfonic acid catalyst, the reaction temperature range may vary from 115° C. (reflux at atmospheric pressure) using a toluene solvent up to 200° C. (reflux, preferably using a toluene or xylene solvent at higher pressures). Thus, the reaction temperature range is considerably greater in scope when using the paratoluene sulfonic acid catalyst than when using the potassium acid sulfate catalyst. Furthermore, the solvent used may be toluene, xylene or a heavy hydrocarbon mineral oil so long as the solvent is inert to the reaction product and is inert to the reactant.

Significantly, the use of the paratoluene sulfonic acid catalyst carries with it a certain definitive advantage over the use of all other dehydration catalysts including the potassium acid sulfate; that is, the versatility of equipment that can be used with paratoluene sulfonic acid as opposed to, for example, potassium acid sulfate. The paratoluene sulfonic acid catalyst's use gives rise to insignificant corrosion problems when using steel reactors. Thus, when using a paratoluene sulfonic acid catalyst, the need for using glass-lined equipment or glass-lined reactors is obviated thereby significantly reducing the capital equipment cost in the establishment of a plant for producing the farnesene isomer mixtures of this invention. On the other hand, when using the potassium acid sulfate catalyst, although this catalyst gives rise to useful, unobvious and advantageous products, it is necessary to devise such equipment whereby little corrosion takes place during the course of the reaction. Such equipment will necessarily be either stainless steel or, more preferably, glass-lined equipment with appropriate accessories. When carrying out these reactions in a continuous fashion, it is much more important to design equipment whereby the corrosion incidence will be minimal thereby requiring specific low acid environment corrosion type alloys. The situation concerning the use of continuous equipment gives rise to an even greater need to use either specific alloys when utilizing a potassium acid sulfate catalyst or utilizing a paratoluene sulfonic acid catalyst whereby standard continuous steel processing equipment may be utilized.

Significantly, whether using a potassium acid sulfate catalyst or a paratoluene sulfonic acid catalyst, no nerolidol acetates will be formed which is the case when using, for example, an acetic anhydride dehydration catalyst. The structures of the nerolidol esters are, when using an acetic anhydride catalyst:

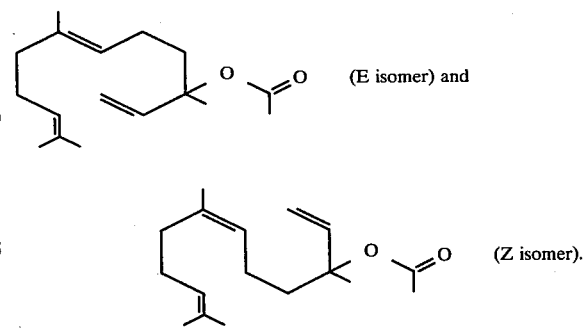

Whether using a potassium acid sulfate catalyst or a paratoluene sulfonic acid catalyst, the ratio of catalyst to nerolidol may vary from 1:1000 (wt/wt) up to 1:5 with a preferred ratio of 1:60 when using the potassium acid sulfate catalyst and a preferred ratio of 1:500 when using the paratoluene sulfonic acid catalyst. The concentration of catalyst in the reaction mixture may vary from 1:2000 up to 1:100 with a preferred ratio of between 1:800 and 1:1,500 (wt/wt) being optimum.

The ratio of solvent:nerolidol isomer mixture varies depending upon the particular solvent used and the desired catalyst concentration. Thus, when using a heavy hydrocarbon inert mineral oil and a potassium acid sulfate catalyst, the preferred ratio of solvent-:nerolidol isomer reactants is between 1:1 and 1:4 with a most preferred ratio being 1:3. When using a toluent solvent or a xylene solvent, the preferred weight/weight ratio may vary from 1:2 up to 2:1 with a most preferred weight ratio of nerolidol isomer mixture:solvent being 1:1.

The product-by-process of our invention, the farnesene isomer mixture, and one or more auxiliary perfume ingredients including, for example, alcohols, aldehydes, ketones, nitriles, esters, cyclic esters (lactones), dialkyl ethers, alkyl alkenyl ethers, thioethers, thiols, carboxylic acids and hydrocarbons other than the farnesene isomeric mixture of our invention and natural essential oils may be admixed so that the combined odors of the individual components produce a pleasant and desired fragrance, particularly and preferably in wet petal, white flower fragrances, e.g., magnolia, gardenia and tuberose. Such perfume compositions usually contain (a) the main note or the "bouquet" or foundation stone of the composition; (b) modifiers which round off and accompany the main notes; (c) fixatives which include odorous substances which lend a particular note to the perfume throughout all states of evaporation and substances which retard evaporation; and (d) top notes which are usually low-boiling, fresh-smelling materials.

In perfume compositions, it is the individual components which contribute to their particular olfactory characteristics, however, the overall sensory effect of the perfume composition will be at least the sum total of the effects of each of the ingredients. Thus, the farnesene isomer mixture produced according to the process of our invention can be used to alter, modify or enhance the aroma characteristics of a perfume composition, for example, by utilizing or moderating the olfactory reaction contributed by another ingredient in the composition.

The amount of farnesene isomer mixture of our invention which will be effective in perfume compositions, as well as in perfumed articles and colognes depends on many factors, including the other ingredients, their amounts and the effects which are desired. It has been found that perfume compositions containing as little as 0.01% of the farnesene isomer mixtures or even less (e.g., 0.005%) can be used to impart a very natural waxy, flowery, wet petal (reminiscent of magnolia, tuberose and gardenia) aroma with citrusy (lemon/lime), and petitgrain-like undertones and green top notes to soaps, cosmetics and other products. The amount employed can range up to 70% of the fragrance components and will depend on considerations of cost, nature of the end product, the effect desired on the finished product and the particular fragrance sought.

The farnesene isomer mixture produced according to the process of our invention is useful (taken alone or together with other ingredients in perfume compositions) as (an) olfactory component(s) in detergents and soaps, space odorants and deodorants, perfumes, colognes, toilet waters, bath preparations such as lacquers, brilliantines, pomades and shampoos; cosmetic preparations such as creams, deodorants, hand lotions and sun screens; powders such as talcs, dusting powders, face powders, and perfumed article compositions of matter such as perfumed polypropylene, polyethylene and polyurethanes, partially long-lasting, partially short-lasting mixtures of, for example, encapsulated perfumes suspended in free perfume compositions and the like. When used as (an) olfactory component(s), as little as 0.1% of the farnesene isomer mixture of our invention will suffice to impart an intense, waxy, flowery, wet petal (magnolia-like, tuberose and gardenia-like) aroma with citrusy (lemon/lime), petitgrain-like undertones and green top notes to magnolia, gardenia, tuberose and other white flower formulations. Generally, no more than 3% of the farnesene isomer mixture of our invention based on the ultimate end product is required in the perfume composition.

In addition, the perfume composition or fragrance composition of our invention can contain a vehicle or carrier for the farnesene isomer mixture. The vehicle can be a liquid such as a non-toxic alcohol, (e.g., ethyl alcohol), a non-toxic glycol (e.g., propylene glycol or 1,2-butylene glycol or sorbitol) or the like. The carrier can also be an absorbent solid such as a gum (e.g., gum arabic, xanthan gum or the like) or components for encapsulating the composition (such as gelatin or ethyl cellulose) as by coacervation.

When used as a component of a perfumed article such as a perfumed plastic or a solid or liquid anionic, cationic, nonionic or zwitterionic detergent, or a dryer-added fabric softener article or a fabric softener composition or a shampoo or a soap, the range of farnesene isomer usable varies from 0.005% up to about 5% by weight of the perfumed article. The lower range of this range, e.g., 0.005% up to 0.1% of the farnesene isomer mixture of our invention, is most preferred when using it in a dryer-added fabric softener article or fabric softener composition in view of the need for a "non-perfumy" but pleasant head space aroma above the batch of clothes dried using the dryer-added fabric softener article or fabric softener composition in a standard automatically operated tumbler dryer.

It will thus be apparent that the farnesene isomer mixtures of our invention can be utilized to augment, alter, modify or enhance sensory properties, particularly organoleptic properties, of a wide variety of consumable materials.

Examples I and III, following, serve to illustrate the process for producing the farnesene isomer mixture of our invention usable in practicing Example V and examples following Example V. Example II illustrates a process whereby α-farnesene isomers such as those having the structures:

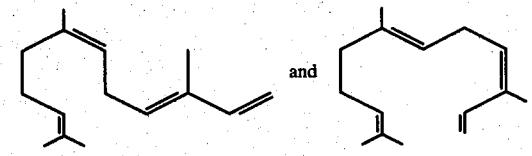

are isolated from the head space of magnolia. Example IV following, illustrates a process unworkable for the purposes of our invention using an acetic anhydride dehydrating agent producing, in addition to farnesene isomer, a mixture of isomers of farnesyl esters.

It will be understood that these examples are illustrative, and the invention is to be considered restricted thereto only as indicated in the appended claims.

All parts and percentages given herein are by weight unless otherwise specified.

EXAMPLE I

PREPARATION OF MIXTURE OF FARNESENE ISOMERS USING A POTASSIUM ACID SULFATE DEHYDRATION CATALYST

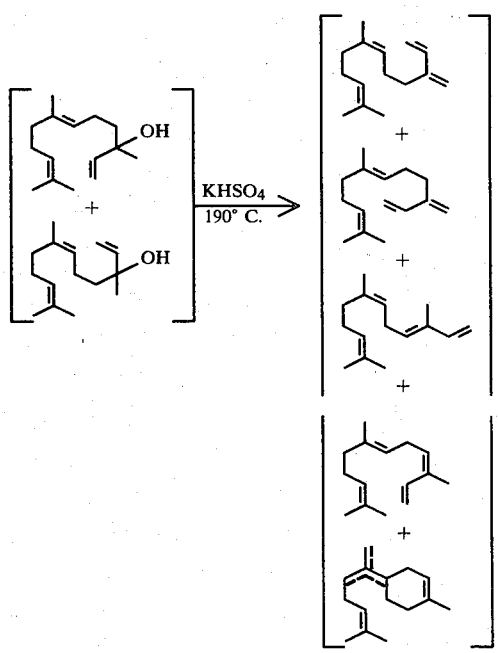

Into a five liter reaction flask equipped with stirrer, Rushover head, 1' splash column with glass packing, thermometer, addition funnel, glass "Y" tube, heating mantle and vacuum set-up, is placed 1000 grams of Primol ® (a mineral oil manufactured by the Exxon Corporation of Linden, N.J.) and 50 grams of potassium acid sulfate (KHSO₄). The resulting mixture is heated to 185° C. and maintained at 185° C. for a period of 15 minutes.

A mixture of nerolidol isomers defined according to the GLC profile set forth in FIG. "A" is placed in the addition funnel and, over a 10 hour period while maintaining the reaction mass temperature at 190° to 195° C. and maintaining a pressure above the reaction mass of 10-15 mm/Hg (vacuum), 3000 grams of the nerolidol isomer mixture is added to the potassium acid sulfate/Primol ® mixture at a rate equal to the rate of condensed distillate. Thus, the distillation of the farnesene isomer mixture is carried out simultaneously with the addition of the nerolidol to the dehydrating medium. The fractions collected are as follows:

| Fraction No. | Vapor Temp °C. | Liquid Temp °C. | Pressure MM Hg. | Wt (g) |
|---|---|---|---|---|
| 1 | 114/127 | 193/188 | 15/15 | 330.3 |
| 2 | 130 | 189 | 15 | 671.4 |
| 3 | 125 | 193 | 15 | 875.9 |
| 4 | 130 | 195 | 15 | 504.2 |
| 5 | 110 | 195 | 15 | 394.2 |
| | | | | 2776.0 g. |

After the addition is completed, the reaction mass is stirred at 190°-200° C. for 1 hour in order to insure complete recovery.

All fractions are bulked, diluted with anhydrous diethyl ether (500 ml), washed with one 1,000 ml portion of 5% sodium carbonate and dried over anhydrous magnesium sulfate. The resulting product is then evaporated on a rotary evaporator whereby the diethyl ether is evaporated.

FIG. 1 is the GLC profile after the base wash. (GLC conditions: 10'×⅛" 5% Carbowax column programmed at 100°-200° C. at 4° C. per minute).

The base washed farnesene bulk (2776.0 grams) is strip distilled using a 2" Splash column containing glass Raschig rings as column packing, yielding the following fractions:

| Fraction No. | Vapor Temp °C. | Liquid Temp °C. | Pressure MM Hg. | Wt (g) |
|---|---|---|---|---|
| 1 | 83/93 | 117/122 | 1/1 | 496.7 |
| 2 | 94 | 123 | 1 | 583.6 |
| 3 | 96 | 128 | 1 | 658.2 |
| 4 | 109 | 139 | 1 | 596.2 |
| 5 | 125 | 205 | 1 | 265.8 |
| | | | | 2600.5 g. |

All fractions are then bulked (2600.5 grams) and fractionated on a 12" vacuum jacketed glass column containing glass Raschig rings as column packing, yielding the following fractions:

| Fraction No. | Vapor Temp °C. | Liquid Temp °C. | Pressure MM Hg. | Reflux Ratio | Wt (g) |
|---|---|---|---|---|---|
| 1 | 46/54 | 135/132 | 1.4/1.0 | 9:1 | 69.5 |
| 2 | 51 | 130 | 0.9 | 9:1 | 87.4 |
| 3 | 52 | 132 | 0.8 | 9:1 | 99.4 |
| 4 | 70 | 133 | 1.4 | 9:1 | 45.1 |
| 5 | 63 | 134 | 0.9 | 9:1 | 109.0 |
| 6 | 53/52 | 127/129 | 0.8/0.7 | 9:1 | 98.4 |
| 7 | 52 | 131 | 0.7 | 9:1 | 136.3 |
| 8 | 51 | 130 | 0.7 | 9:1 | 117.1 |
| 9 | 52 | 133 | 0.7 | 9:1 | 151.2 |
| 10 | 52 | 135 | 0.7 | 9:1 | 166.3 |
| 11 | 62/61 | 133/133 | 0.7/0.7 | 9:1 | 88.8 |
| 12 | 81 | 145 | 2.0 | 9:1 | 68.7 |
| 13 | 71 | 130 | 2.0 | 9:1 | 91.2 |
| 14 | 73 | 132 | 2.0 | 9:1 | 94.1 |
| 15 | 65/73 | 130/131 | 1.2/1.1 | 9:1 | 58.8 |
| 16 | 61 | 129 | 1.2 | 9:1 | 79.1 |
| 17 | 73 | 131 | 1.2 | 9:1 | 141.6 |
| 18 | 62 | 137 | 0.6 | 9:1 | 116.5 |
| 19 | 50/59 | 133/138 | 0.7/0.6 | 9:1/4:1 | 99.8 |
| 20 | 63 | 138 | 0.6 | 3:2 | 119.5 |
| 21 | 45 | 204 | 1.4 | 3:2 | 87.2 |
| | | | | | 2125.0 g |

Fractions 4-18 (1562.2 grams) are bulked.

FIG. 2 is the GLC profile for bulked fractions 4-18.

In FIG. 2, peak 11 indicates the compound having the structure:

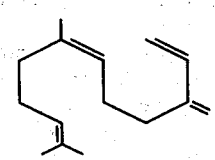

Peak 12 indicates the compound having the structure:

Peak 13 indicates the compound having the structure:

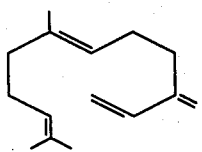

Peak 14 indicates the compounds having the structures:

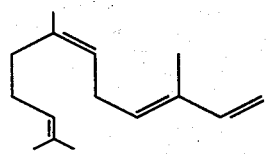

wherein the structure:

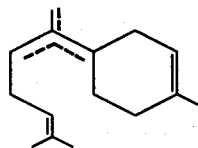

one of the dashed lines represents a pi double bond and each of the other dashed lines represent single bonds. Peaks 15A and 15B are indicative of the compounds having the structures:

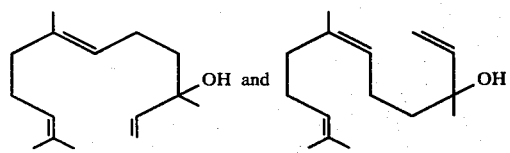

the isomers of nerolidol.

FIGS. 3, 4, 5 and 6 are infra-red spectra of, respectively, peaks 11, 12, 13 and 14 of FIG. 2.

FIGS. 7, 8, 9 and 10 are, respectively, NMR spectra for peaks 11, 12, 13 and 14 of FIG. 2.

FIGS. 11, 12, 13 and 14 are, respectively, mass spectra for peaks 11, 12, 13 and 14 of FIG. 2.

Bulked fractions 14–18 have a very natural waxy, flowery, (magnolia-like, tuberose-like, gardenia-like) aroma with citrusy (lemon/lime), petitgrain-like undertones and green top notes.

EXAMPLE II

ISOLATION OF α-FARNESENE ISOMER MIXTURE FROM MAGNOLIA HEADSPACE

The volatiles of two magnolia blossoms (Cadiz, Spain) were entrained on Carbowax 20 by sweeping the petals with helium for 24 hours. The trap is then analyzed by GLC analysis on a 500'×0.03" SF-96 capillary column.

Figure 16A:
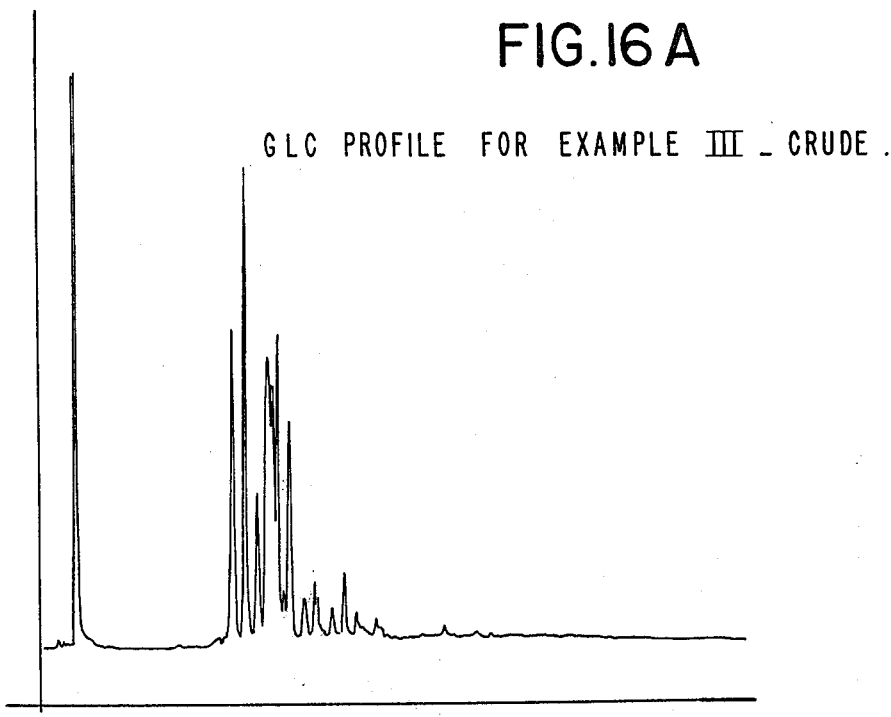
FIG. 16(A) is the GLC profile for the crude reaction product of Example III.
Figure 16B:
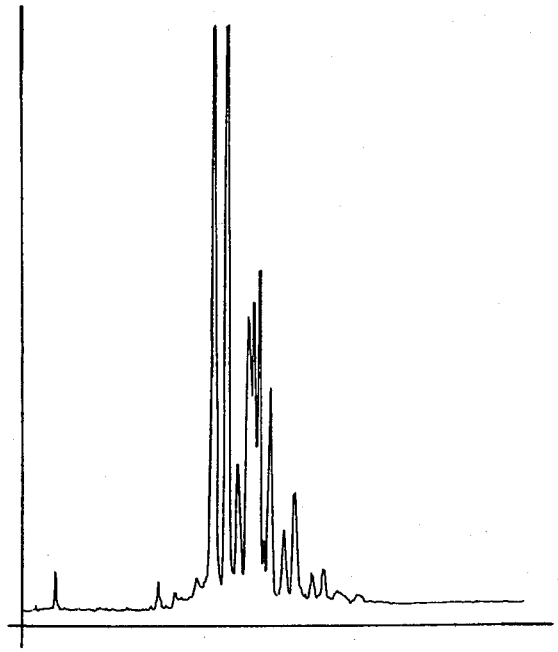
FIG. 16(B) is the GLC profile for fraction 1 of the distillation product of the reaction product of Example III.
Figure 16C:
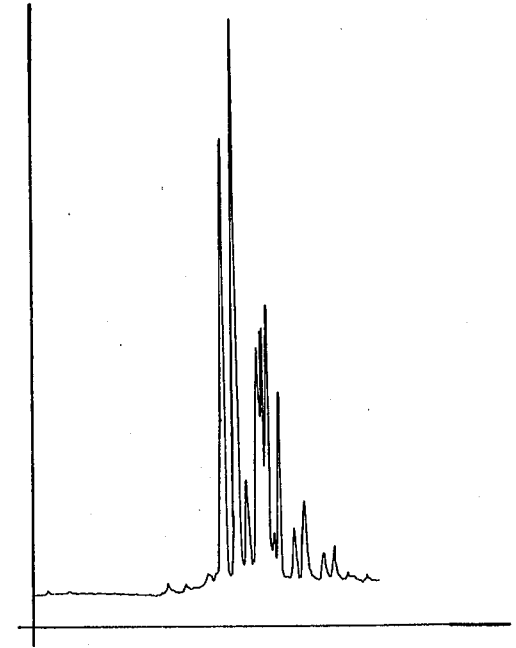
FIG. 16(C) is the GLC profile for fraction 2 of the distillation product of the reaction product of Example III.
Figure 16:
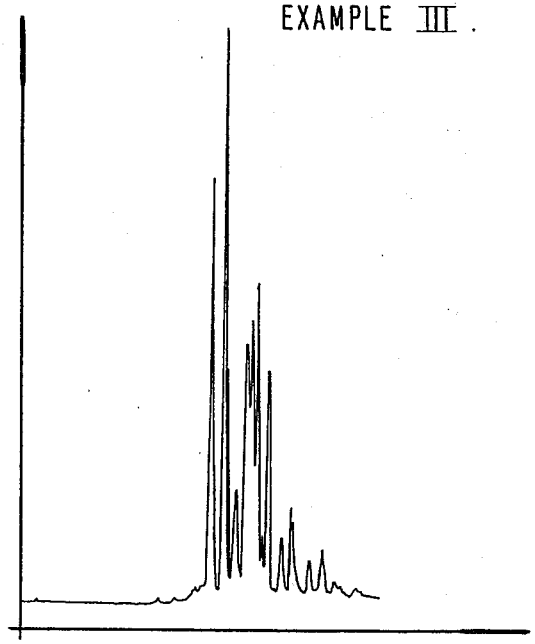
FIG. 16(D) is the GLC profile for fraction 3 of the distillation product of the reaction product of Example III.
FIG. 16(E) is the GLC profile for fraction 4 of the distillation product of the reaction product of Example III.
FIG. 16(F) is the GLC profile for fraction 5 of the distillation product of the reaction product of Example III.
FIG. 16(G) is the GLC profile for fraction 6 of the distillation product of the reaction product of Example III.
FIG. 16(H) is the GLC profile for fraction 7 of the distillation product of the reaction product of Example III.
FIG. 16(J) is the GLC profile for fraction 8 of the distillation product of the reaction product of Example III.
FIG. 16(K) is the GLC profile for fraction 9 of the distillation product of the reaction product of Example III.
FIG. 16(L) is the GLC profile for bulked fractions 4-7 of the distillation product of the reaction product of Example III.
Figure 16:
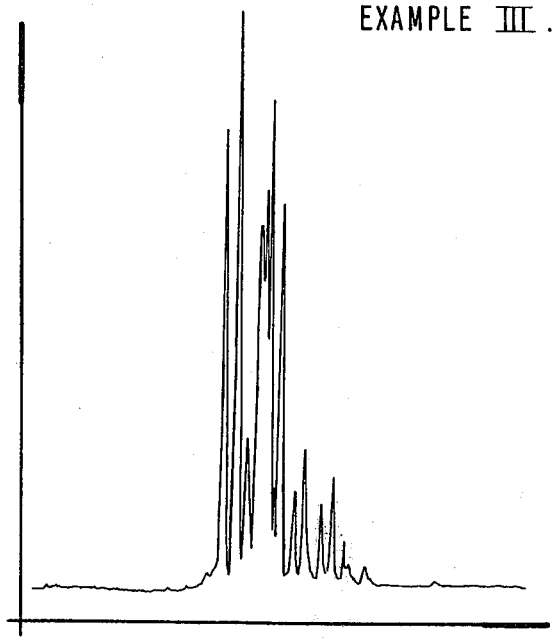
Figure 16:
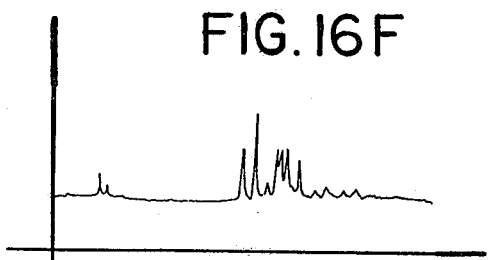
Figure 16:
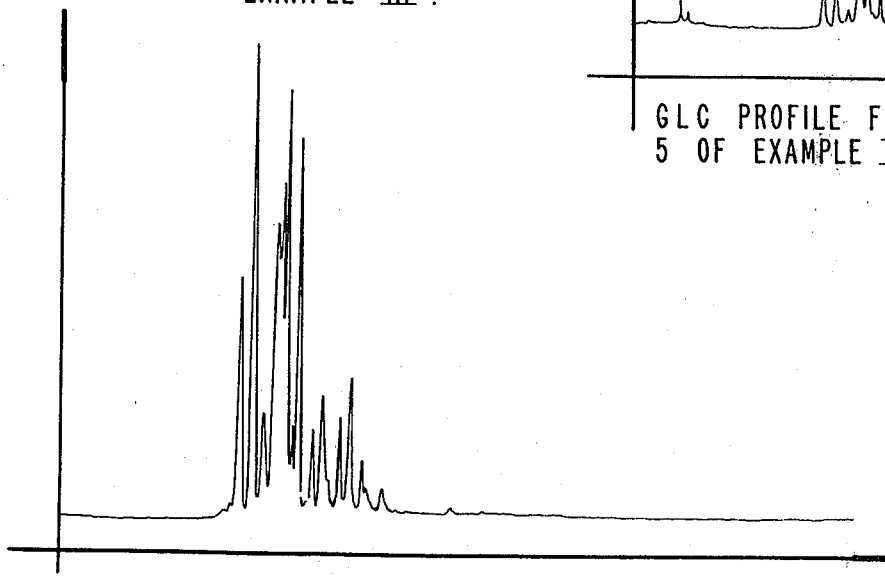

FIG. 16 is the GLC profile for this headspace. Reference numeral 16 is indicative of the α-farnesene isomers contained in the headspace. Such α-farnesene isomers are represented by the structures:

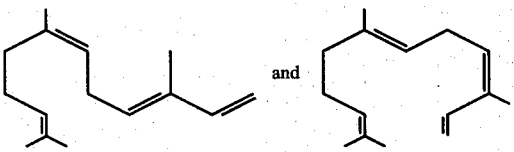

EXAMPLE III

PREPARATION OF ISOMERIC FARNESENE MIXTURE FROM NEROLIDOL MIXTURE USING PARATOLUENE SULFONIC ACID CATALYST

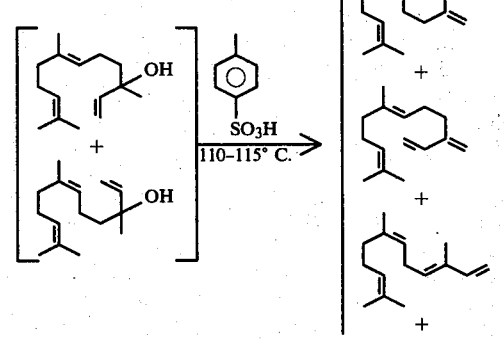

(wherein in the structure:

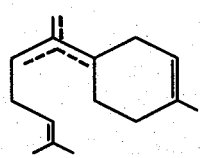

one of the dashed lines is indicative of a pi double bond and each of the other of the dashed lines is indicative of single bonds, said structure:

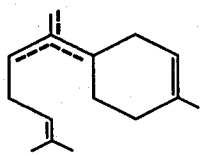

being indicative of a mixture of three compounds).

Into a two liter, three-neck reaction flask equipped with mechanical stirrer, reflux condenser, Bidwell water separater, thermometer and heating mantle is added 500 grams of a nerolidol isomer mixture containing compounds having the structures:

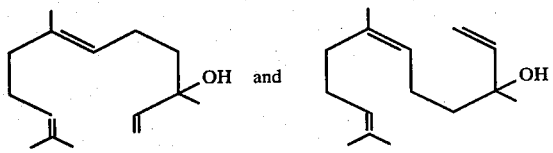

defined more specifically according to the GLC profile of FIG. B, and one gram of paratoluene sulfonic acid.

The reaction mass is stirred at room temperature for a period of 2 hours. The reaction mass is then refluxed for a period of 3 hours until 40 ml of water is removed. The reaction mass is then washed with one portion of 200 ml of 5% sodium carbonate and two 100 ml portions of water. The resulting organic layer is dried over anhydrous magnesium sulfate, filtered and the solvent is removed at atmospheric pressure.

The crude reaction mass is then analyzed on a GLC column.

FIG. 16(A) is the GLC profile for the crude product. (Conditions: 10'×⅛" 5% Carbowax column programmed at 100°–240° C. at 4° C. per minute.)

The crude reaction mass is then distilled using a 4" column containing glass rings as packing and a Rushover head.

The distillation fractions are as follows:

| Fraction Number | Vapor Temp. (°C.) | Liquid Temp. (°C.) | Pressure mm/Hg. | Weight of Fraction (grams) |
| --- | --- | --- | --- | --- |
| 1 | 82/85 | 103/104 | 1.8/1.8 | 22.8 |
| 2 | 87 | 104 | 1.8 | 33.6 |
| 3 | 89 | 105 | 1.8 | 51.3 |
| 4 | 89 | 108 | 1.8 | 51.1 |
| 5 | 90 | 111 | 1.8 | 50.6 |
| 6 | 90 | 115 | 1.8 | 46.6 |
| 7 | 92 | 118 | 1.8 | 51.1 |
| 8 | 94 | 155 | 1.8 | 22.4 |
| 9 | 100 | 200 | 1.8 | 11.5 |

Fractions 4–7 are bulked. These fractions have a pleasant waxy, flowery (magnolia-like, tuberose-like, gardenia-like), wet petal aroma with citrusy (lemon/lime) petitgrain-like undertones and green top notes.

FIG. 16(B) is the GLC profile for fraction 1 of the foregoing distillation (conditions: 10'×⅛" 5% Carbowax column programmed at 100°–220° C. at 4° C. per minute). The conditions for the following GLC analysis are the same.

Figure 16H:
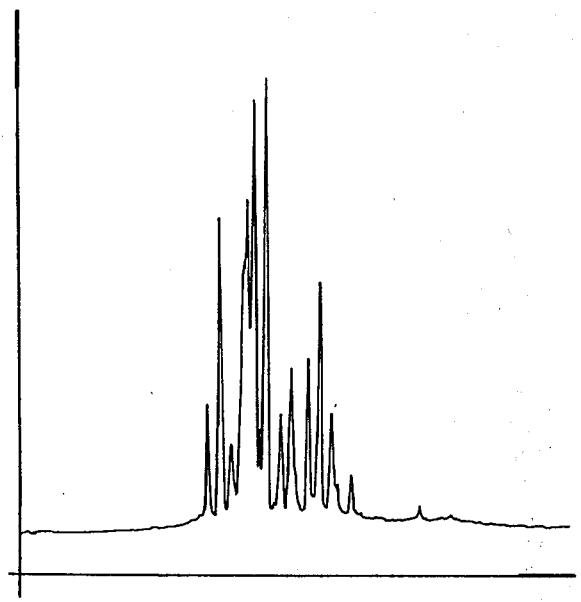
Figure 16J:
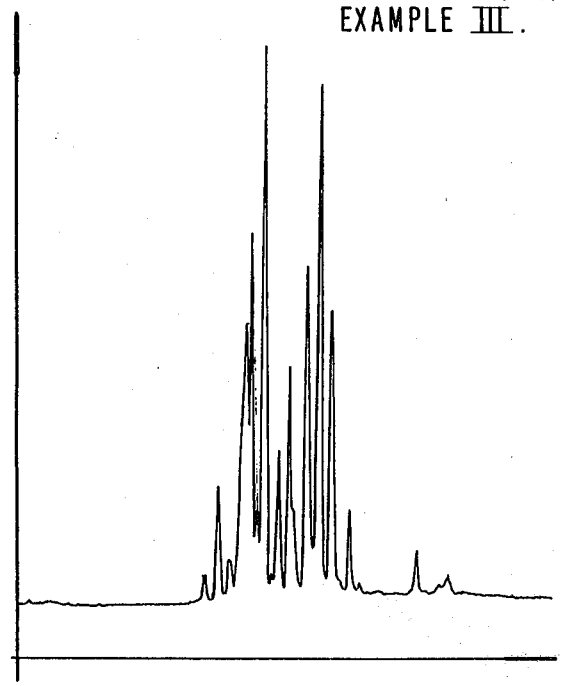
Figure 16K:
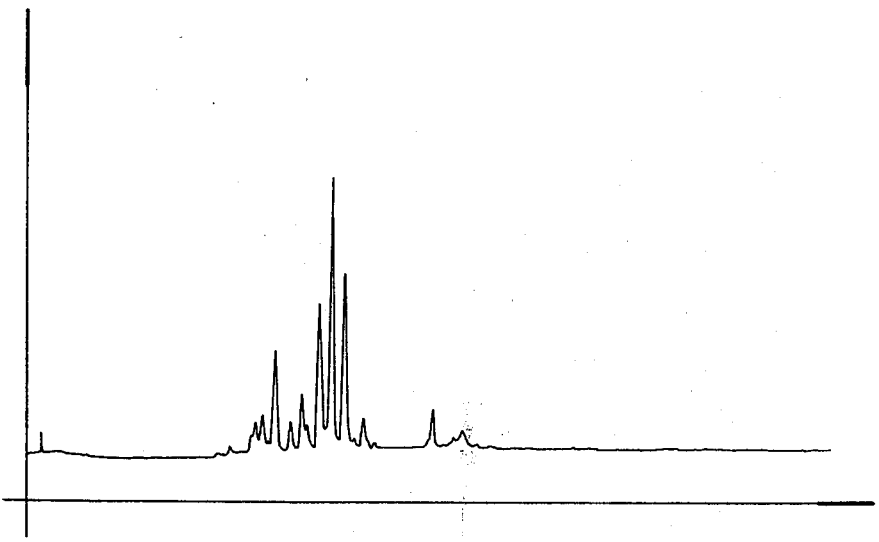
Figure 16L:
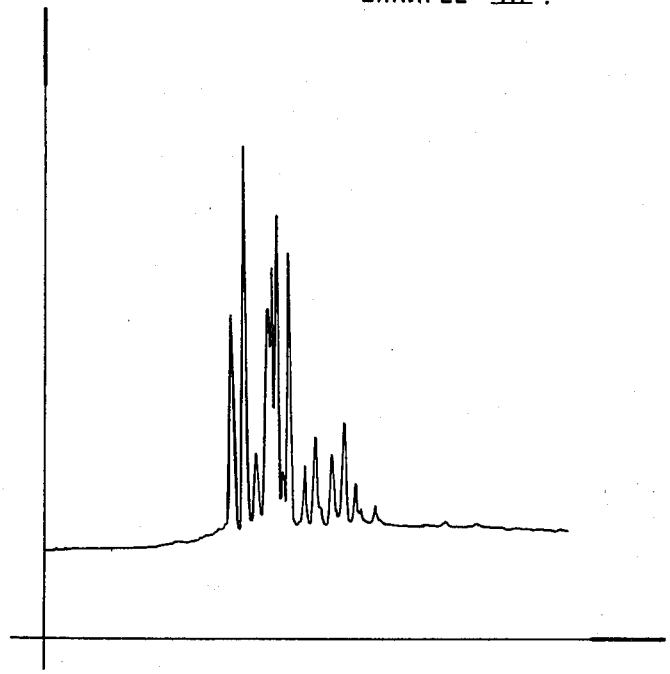

FIG. 16(C) is the GLC profile for fraction 2.
FIG. 16(D) is the GLC profile for fraction 3.
FIG. 16(E) is the GLC profile for fraction 4.
FIG. 16(F) is the GLC profile for fraction 5.
FIG. 16(G) is the GLC profile for fraction 6.
FIG. 16(H) is the GLC profile for fraction 7.
FIG. 16(J) is the GLC profile for fraction 8.
FIG. 16(K) is the GLC profile for fraction 9.
FIG. 16(L) is the GLC profile for bulked fractions 4–7.

Figure 17:
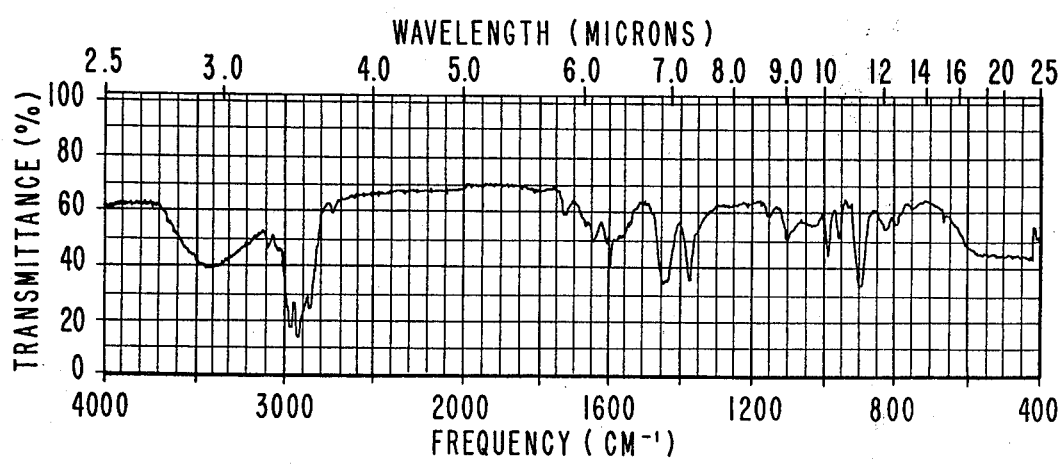
FIG. 17 is the infra-red spectrum for bulked fractions 4-17 of the distillation product of the reaction product of Example III.

FIG. 17 is the infra-red spectrum for bulked fractions 4–7 of the foregoing distillation.

EXAMPLE IV

ATTEMPTED PREPARATION OF ODOR ACCEPTABLE MIXTURE OF FARNESENE ISOMERS USING ACETIC ANHYDRIDE DEHYDRATION REAGENT

Into a one-liter distillation flask equipped with thermometer, condenser, separatory funnel (containing dry ice), magnetic stirrer and heating mantle under a nitrogen atmosphere is placed 200 grams of nerolidol, a 65:35 mixture of the isomers having the structures:

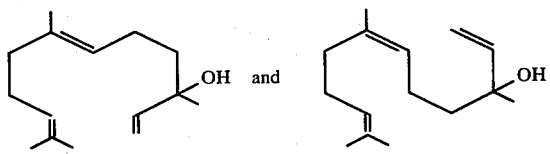

obtained from the Givaudan Corporation of Clifton, N.J. and 500 ml acetic anhydride. The reaction mass is refluxed at 130°–140° C. for a period of 4 hours.

The reaction mass is then added to 300 grams of ice in a separatory funnel.

The organic layer and the aqueous layer are separated. The organic layer is washed with a 10% solution of sodium carbonate followed by saturated sodium chloride solution. The organic layer is dried over anhydrous magnesium sulfate and the solvent is evaporated on a rotary evaporator.

The weight of the crude material is 237.8 grams.

The resulting crude material is distilled on a Spinning Band column yielding the following fractions:

| Fraction Number | Vapor Temp. (°C.) | Liquid Temp. (°C.) | Pressure mm/Hg. | Weight of Fraction (grams) |
| --- | --- | --- | --- | --- |
| 1 | 88/101 | 148/150 | 20/20 | 2.0 |
| 2 | 102 | 151 | 20 | 3.2 |
| 3 | 103 | 151 | 20 | 3.0 |
| 4 | 102 | 151 | 19 | 2.4 |
| 5 | 106 | 159 | 20 | 3.8 |
| 6 | 111 | 151 | 20 | 3.5 |
| 7 | 115 | 155 | 20 | 3.4 |
| 8 | 70 | 160 | ? | 2.5 |
| 9 | 103/112 | 161/161 | 20/20 | 3.6 |
| 10 | 111 | 161 | 20 | 3.6 |
| 11 | 110 | 161 | 20 | 3.6 |
| 12 | 106 | 166 | 20 | 3.2 |
| 13 | 93 | 166 | 20 | 3.1 |
| 14 | 93 | 166 | 20 | 3.1 |
| 15 | 102 | 168 | 20 | 2.3 |
| 16 | 102 | 168 | 20 | 2.7 |
| 17 | 100 | 170 | 20 | 2.4 |

Fractions 6–12 are then re-distilled on a Micro-Vigreux column to yield the following fractions:

| Fraction Number | Vapor Temp. (°C.) | Liquid Temp. (°C.) | Pressure mm/Hg. | Weight of Fraction (grams) |
|---|---|---|---|---|
| 1 | 83/111 | 95/115 | 1.1/0.9 | 3.0 |
| 2 | 105 | 113 | 0.5 | 3.3 |
| 3 | 95 | 110 | 0.5 | 2.2 |
| 4 | 85 | 98 | 0.5 | 2.7 |
| 5 | 76 | 93 | 0.5 | 1.9 |
| 6 | 78 | 98 | 0.5 | 2.3 |
| 7 | 79 | 98 | 0.5 | 2.4 |
| 8 | 75 | 110 | 0.5 | 2.1 |
| 9 | 50 | 190 | 0.5 | 0.6 |

Fractions 4–8 are bulked and odor evaluated.

FIG. 18 is the GLC profile for the crude reaction product (conditions: 10′×⅛″ 5% Carbowax column programmed at 220° C. isothermal).

FIG. 19 is the GLC profile for bulked fractions 4–8 of the foregoing distillation (conditions: 10′×⅛″ 5% Carbowax column programmed at 200° C. isothermal).

In FIG. 18, peaks 17A and 17B are indicative of farnesene isomers whereas peaks 18A, 18B and 18C are indicative of farnesyl acetate isomers as indicated by the structures:

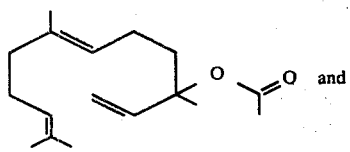

and

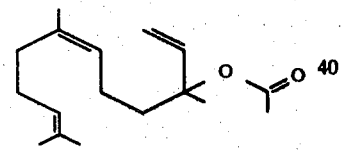

More particularly, in FIG. 19, peak 19A signifies the compound having the structure:

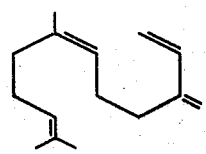

Peak 19B signifies the compound having the structure:

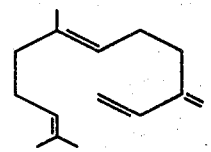

Peak 19C signifies the compound having the structure:

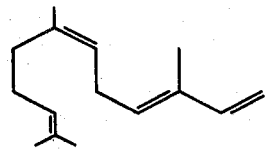

Peak 19D signifies the compound having the structure:

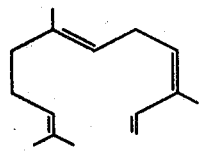

Insofar as the proportions of isomers in fractions 1–9 are concerned, these are as follows:

| Fraction Number | Weight (grams) | Peak 19A | Peak 19B | Peak 19C | Peak 19D |
|---|---|---|---|---|---|
| 1 | 3.0 | 10.8 | 22.8 | 16.1 | 31.4 |
| 2 | 3.3 | 9.6 | 21.6 | 16.5 | 33.5 |
| 3 | 2.2 | 8.3 | 20.4 | 16.6 | 36.0 |
| 4 | 2.7 | 8.0 | 20.0 | 16.6 | 37.0 |
| 5 | 1.9 | 7.6 | 19.6 | 16.7 | 37.5 |
| 6 | 2.3 | 6.1 | 17.5 | 16.4 | 38.4 |
| 7 | 2.4 | 4.4 | 15.1 | 17.0 | 44.7 |
| 8 | 2.1 | 2.9 | 11.7 | 16.0 | 49.0 |
| 9 | 0.6 | 1.3 | 7.6 | 13.4 | 49.0 |

The resulting bulked fractions 4–8 have a fresh, smooth, rosy, citrus note. The citrus part has a lemon/lime/petitgrain aroma which is very intense. Also present are strong terpenic notes. The material has none of the "wet petal", "white flower" aroma nuances produced according to Examples I and III. In addition, the material produced according to the instant example has fatty, orangy, licorice-like, and metallic undertones which cause it to lack usefulness in substantially all perfumery areas and all perfumed article areas.

EXAMPLE V

ELUCIDATION OF RANGE OF OPERABLE VARIABLES OF INVENTION

EXAMPLE V(A)

PRODUCTION OF FARNESENE ISOMER MIXTURE USING POTASSIUM ACID SULFATE CATALIST AT 150° C.

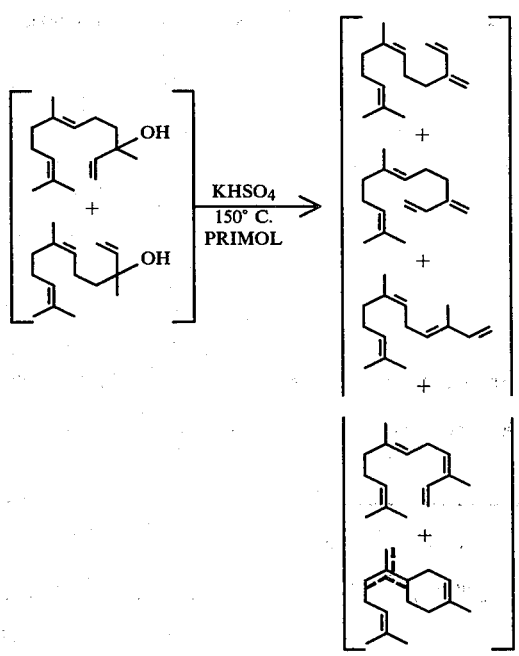

Into a three liter reaction vessel equipped with 6" Splash column Rushover head, mechanical stirrer, addition funnel, thermometer, and fraction cutter, is placed 500 grams Primol and 50 grams potassium acid sulfate (KHSO₄). The mixture is heated to 190° C. while keeping the system under 5 mm/Hg vacuum.

The resulting mixture is maintained at 190° C. for 30 minutes in order to "melt" the potassium acid sulfate crystals.

The resulting mixture is then cooled to 150° C. and over a period of 6 hours nerolidol having a GLC profile as set forth in FIG. A is added to the reaction mass dropwise from the addition funnel. The isomers of nerolidol in the nerolidol reactant are:

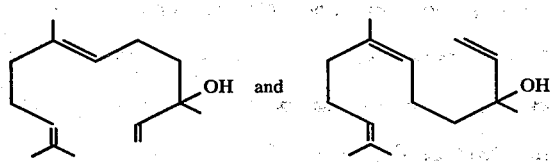

The addition rate of the nerolidol is adjusted to equal the "take off rate" of the product. After the addition is completed, the heating is continued until no additional liquid is distilled.

The reaction mass is then rinsed with toluene into a separatory funnel. The resulting organic layer is washed with 1 volume of 5% sodium carbonate and 2 volumes of water. The organic layer is then dried over anhydrous magnesium sulfate and stripped distilled and rushed over yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 74/90 | 92/97 | 3 | 75.4 |
| 2 | 91 | 98 | 2 | 79.3 |
| 3 | 92 | 100 | 2 | 92.9 |
| 4 | 93 | 100 | 2 | 81.7 |
| 5 | 93 | 100 | 2 | 86.5 |
| 6 | 96 | 104 | 2 | 88.0 |
| 7 | 99 | 106 | 2 | 88.0 |
| 8 | 101 | 108 | 2 | 95.2 |
| 9 | 103 | 109 | 2 | 86.9 |
| 10 | 103 | 109 | 2 | 89.1 |
| 11 | 103 | 109 | 2 | 83.9 |
| 12 | 103 | 112 | 2 | 85.7 |
| 13 | 103 | 114 | 2 | 81.5 |
| 14 | 112 | 145 | 2 | 86.3 |
| 15 | 155 | 210 | 2 | 51.3 |

Fractions 7-11 are bulked and have a waxy, flowery, wet petal aroma reminiscent of magnolia, tuberose, and gardenia with jasmin top notes.

EXAMPLE V(B)

ATTEMPTED PRODUCTION OF FARNESENE ISOMERS USING CYCLOHEXANE SOLVENT AND POTASSIUM ACID SULFATE CATALYST

Into a 3 liter reaction flask equipped with thermometer, condenser, bidwell trap, mechanical stirrer and heating mantle is placed 1000 grams (4.5 moles) of nerolidol having a GLC profile in accordance with FIG. A, 20.0 grams of potassium acid sulfate and 600 ml cyclohexane. The resulting mixture is heated to reflux and 4.5 moles (80 grams) of water are collected. The refluxing proceeds for a period of 4 hours. At the end of the refluxing, the reaction mass is washed with 1 volume of 5% sodium carbonate and 1 volume of water. The reaction mass is then dried over anhydrous magnesium sulfate and stripped atmospherically to yield 920 grams of crude product. The resulting crude product is then distilled on a 2 liter-short Splash column packed with saddles to yield the following fractions:

| Fraction Number | Vapor Temp. (°C.) | Liquid Temp. (°C.) | Pressure mm/Hg. | Weight of Fraction (grams) |
|---|---|---|---|---|
| 1 | 78/87 | 101/108 | 0.95/0.90 | 78.7 |
| 2 | 88 | 111 | 0.90 | 83.8 |
| 3 | 89 | 111 | 0.9 | 82.5 |
| 4 | 89 | 115 | 0.9 | 100.8 |
| 5 | 89 | 126 | 0.9 | 95.1 |
| 6 | 112 | 158 | 0.9 | 85.5 |
| 7 | 120 | 181 | 1.1 | 83.2 |
| 8 | 120 | 205 | 1.1 | 94.6 |
| 9 | 123 | 214 | 1.1 | 68.6 |
| 10 | 112 | 225 | 1.0 | 32.5 |

The resulting product has a terpenic character and is unsuitable for use in perfumery. It does not have the "wet petal", waxy, flowery aroma found in the reaction product of Example V(A), I or III.

EXAMPLE V(C)

ATTEMPTED PRODUCTION OF FARNESENE ISOMERS USING TOLUENE SOLVENT AND POTASSIUM BISULFATE DEHYDRATING CATALYST

Into a 5 liter reaction flask equipped with mechanical stirrer, heating mantle, thermometer, bidwell trap and reflux condenser is placed 1000.0 grams (4.5 moles) of nerolidol having a GLC profile according to FIG. A, 600 ml tolune and 16.7 grams of potassium bisulfate (KHSO$_4$). The resulting mixture is heated to reflux (110° C.) and heating is continued until the theoretical amount of water, 81 grams (4.5 moles) are collected.

The water take-off proceeds for a period of 5.5 hours.

The reaction mass is then transferred to a 5 liter separatory funnel and 1000 ml of 5% sodium carbonate solution are added in order to wash the product. The organic and aqueous layers are then separated and the organic layer is dried over anhydrous magnesium sulfate. The resulting product is then filtered by gravity into a 3 liter distillation flask and rushed over on a short splash column packed with glass Raschig rings yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 25/30 | 40/68 | 20/5 | 107.1 |
| 2 | 98 | 112 | 2 | 99.5 |
| 3 | 100 | 115 | 2 | 103.4 |
| 4 | 100 | 117 | 2 | 103.0 |
| 5 | 100 | 120 | 2 | 85.6 |
| 6 | 100 | 128 | 2 | 99.9 |
| 7 | 100 | 138 | 2 | 98.5 |
| 8 | 108 | 179 | 2 | 63.8 |
| 9 | 110 | 205 | 2 | 85.9 |
| 10 | 150 | 225 | 2 | 37.9 |

The resulting product is then redistilled on an 18" glass column packed with Raschig rings to yield the following fractions:

| Fraction Number | Vapor Temp. (°C.) | Liquid Temp. (°C.) | Pressure mm/Hg. | Weight of Fraction (grams) |
|---|---|---|---|---|
| 1 | 64/68 | 113/120 | 1.2/1.1 | 42.7 |
| 2 | 70 | 121 | 1.1 | 60.4 |
| 3 | 70 | 122 | 1.0 | 77.3 |
| 4 | 73 | 127 | 1.1 | 64.6 |
| 5 | 74 | 128 | 1.1 | 80.9 |
| 6 | 76 | 130 | 1.2 | 93.6 |
| 7 | 85 | 135 | 1.6 | 88.4 |
| 8 | 78/84 | 138/140 | 1.1/1.1 | 38.9 |
| 9 | 92 | 177 | 1.0 | 93.3 |
| 10 | 93 | 215 | 1.6 | 54.3 |

The resulting product and each of the individual fractions are each incapable of being useful in perfumery in view of their terpinic, nerolidol-like character.

EXAMPLE VI

MAGNOLIA FORMULATION

To demonstrate the use of the farnesene isomer mixture produced according to Examples I, III and V(A) in a magnolia formulation, the following formula is provided:

| Ingredients | Parts by Weight |
|---|---|
| Phenylethyl alcohol | 200 |
| Geraniol | 400 |
| Trichloromethylphenyl carbinyl acetate | 20 |
| Phenylethyl acetate | 60 |
| Undecylenic aldehyde (10% in diethyl phthalate) | 5 |
| n-nonyl aldehyde (10% in diethyl phthalate) | 2 |
| Musk ketone | 10 |
| Musk ambrette | 10 |
| Eugenol phenyl acetate | 20 |
| Citronellol | 100 |
| Vanillin (10% in diethyl phthalate) | 6 |
| Eugenol | 30 |
| Citronellyl formate | 30 |
| Geranyl acetate | 10 |
| Linalool | 40 |
| Geranyl phenyl acetate | 50 |
| Cis beta, γ-hexenyl acetate | 2 |
| 1-(2,5,5-trimethyl-1,3-cyclohexadien-1-yl)-1,3-butanedione | 5 |
| Farnesene isomer mixture produced according to either of Example I, III or V(A) | 180 |

The addition of the farnesene isomer mixture of either of Examples I, III or V(A) lends a great deal of strength and character to the magnolia fragrance imparting to it a waxy, flowery aroma with an intense wet petal character reminiscent of white flowers. At lower concentrations, the farnesene isomer mixtures are more subtle, however, they still yield an interesting natural effect with the white flower, waxy, wet petal undertone.

EXAMPLE VII

PREPARATION OF A SOAP COMPOSITION

One hundred grams of soap chips are produced according to Example V of U.S. Pat. No. 4,058,487 issued on Nov. 15, 1977 as follows:

The sodium salt of an equal mixture of $C_{10}$–$C_{14}$ alkane sulfonates (95% active), 40 pounds, is dissolved in a mixture of 80 pounds of anhydrous isopropanol and 125 pounds of dionized water at 150° F. In this mixture is dissolved 10 pounds of partially hydrogenated coconut oil, fatty acids and 15 pounds of sodium mono-$C_{14}$-alkylmaleate and the pH of the solution is adjusted to 6.0 by the addition of a small amount of a 50% aqueous solution of sodium hydroxide. The isopropanol is distilled off and the remaining aqueous solution is drum dried. The resulting solid actives are then blended in a chip mixture with 10 pounds of water, 0.2 pounds titanium hydroxide and 0.75 pounds of one of the materials set forth in Table I below:

TABLE I

| Perfume Ingredient | Aroma Profile |
|---|---|
| Perfume material of Example VI | An intense, magnolia aroma with pleasant wet petal, waxy and flowery nuances and an extremely natural character. |
| One of the farnesene isomer mixtures produced according to Example I, III or V(A) | A waxy, flowery, natural white flower (tuberose, magnolia, jasmin and gardenia) aroma with interesting wet petal characteristics. |

The chips are then plodded into logs, cut to size and finally stamped into bars, having a pH of approximately 6.9.

Each of the perfumed soaps of Table I above manifests an excellent characteristic as indicated in Table I above.

EXAMPLE VIII

PREPARATION OF A DETERGENT COMPOSITION

A total of 100 grams of a detergent powder prepared according to U.S. Pat. No. 4,058,472 and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ alkyl catechol, 35% of sodium tetrapyrophosphate, 30% of sodium silicate, 20% of sodium carbonate, 3% of sodium carboxymethyl cellulose and 7% of starch is mixed with 0.15 grams of one of the perfume ingredients of Table I of Example VII, supra, until a substantially homogeneous composition is obtained. This composition has an excellent aroma as indicated according to Table I of Example VII, supra.

EXAMPLE IX

PREPARATION OF COSMETIC POWDER COMPOSITIONS

A cosmetic powder is prepared by mixing in a ball mill 100 grams of talcum powder with 0.25 grams of one of the perfume materials of Table I of Example VII, supra. Each of the cosmetic powders has an excellent aroma as set forth in Table I of Example VII, supra.

EXAMPLE X

PERFUMED LIQUID DETERGENTS

Concentrated liquid detergents having aromas as set forth in Table I of Example VII, supra, are prepared by adding 0.10%, 0.15% and 0.20% of each of the perfume ingredients of Table I of Example VII, supra. They are prepared by adding and homogeneously mixing the appropriate quantity of perfume material in the liquid detergent. The detergents all possess aromas as set forth in Table I of Example VII, supra.

EXAMPLE XI

PREPARATION OF COLOGNE AND HANDKERCHIEF PERFUMES

Each of the compositions of Table I of Example VII, supra, is incorporated into colognes at several concentrations, 2.0%, 2.5%, 3.0%, 3.5%, 4.0%, and 5.0% in 70%, 75%, 80%, 85% and 90% aqueous ethanol; and into handkerchief perfumes at concentrations of 10%, 15%, 20% and 25% (in 80%, 85%, 90% and 95% aqueous ethanol). The use of each of the perfume ingredients as set forth in Table I of Example VII, supra, affords distinctive aromas as set in Table I of Example VII, supra.

EXAMPLE XII

PREPARATION OF A DETERGENT COMPOSITION

A total of 100 grams of a detergent powder (a non-ionic detergent powder containing a proteolytic enzyme prepared according to Example I of Canadian Patent No. 985,190 issued on Mar. 9, 1976) is mixed with 0.15 grams of a perfume material set forth in Table I of Example VII, supra, until a substantially homogeneous composition is obtained in each case. Each of the compositions has an excellent aroma as set forth in Table I of Example VII, supra.

EXAMPLE XIII

Utilizing the procedure of Example I at column 15 of U.S. Pat. No. 3,632,396 (which is hereby incorporated by reference into the instant specification), a nonwoven cloth substrate useful as a dryer-added fabric softening article of manufacture is prepared wherein the substrate, the substrate coating and the outer coating and the perfume material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS
   22% isopropyl alcohol
   20% antistatic agent
   1.5% of one of the perfume materials of Table I of Example VII, supra.

A fabric softening composition prepared as set forth above having an aroma characteristic as set forth in Table I of Example VII, supra, consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and an outer coating weight ratio of about 1:1 by weight of the substrate. The resulting aromas can be described as set forth in Table I of Example VII, supra, and are imparted in pleasant manners to the head space in the dryer on operation thereof using said dryer-added fabric softening nonwoven fabric.

EXAMPLE XIV

PERFUMED POLYETHYLENE

Scented polyethylene pellets having a pronounced aroma as set forth in Table I of Example VII, supra, are prepared as follows (in accordance with Example III of U.S. Pat. No. 3,505,432 which is incorporated by reference herein):

75 pounds of polyethylene of a melting point of about 220° F. are heated to about 230° F. in a container as illustrated in FIGS. 1 and 2 of U.S. Pat. No. 3,505,432. 25 pounds of one of the perfume materials of Table I of Example VII, supra, are then quickly added to the liquified polyethylene, the lid is put in place and the agitating means are actuated. The temperature is maintained at about 225° F. and the mixing is continued for about 15 minutes. The valve is then opened to allow flow of the molten polyethylene enriched with the perfume containing material to exit through the orifices as indicated in FIGS. 1 and 2. The liquid falling through the orifices solidifies almost instantaneously upon impact with the moving cooled conveyor. Solid polyethylene beads or pellets having a pronounced aroma as set forth in Table I of Example VII, supra, are thus formed. Analysis demonstrates that the pellets contain about 25% of the perfume substance of Table I of Example VII, supra, so that almost no losses of the scenting substance occur. These pellets may be called master pellets. 50 pounds of the perfume substance containing master pellets are then added to 1000 pounds of unscented polyethylene powder and the mass is heated to the liquid state. The liquid is molded into thin sheets or films. The sheets or films have a pronounced aroma as set forth in Table I of Example VII, supra.

EXAMPLE XV

SCENTED POLYPROPYLENE 100 pounds of polypropylene are heated to about 300° F. 30 pounds of one of the aroma materials of Table I of Example VII, supra, are added to the liquified polypropylene. The procedure is carried out in the apparatus of FIGS. 1 and 2 of U.S. Pat. No. 3,505,432. After mixing for about 8 minutes, the valve is opened to allow the exit of the polypropylene-scented material mixture whereby solid pellets having a pronounced aroma as set forth in Table I of Example VII, supra, are formed on the conveyor. The pellets thus obtained are then admixed with about 20 times their weight of unscented polypropylene and the mixture is heated and molded into flat discs. The flat discs have a strong and pleasant aroma as set forth in Table I of Example VII, supra.

EXAMPLE XVI

A perfumed polymer is produced by admixing a microporous polymer produced according to one of Examples 194–236 of U.S. Pat. No. 4,247,498 (the disclosure of which is incorporated by reference herein), and applying a 0.5 mm/Hg vacuum to the system. The resulting product is then compressed into pellets and molded into fragrance-emitting plastic objects, e.g. automobile dashboards.

What is claimed is:

1. A process for augmenting or enhancing the aroma of the head space above a dried batch of clothing comprising the step of adding to the clothing batch prior to drying and during the washing cycle a drier-added fabric softener article having previously added thereto an aroma augmenting or enhancing quantity of a farnesene isomer mixture produced according to the process of dehydrating a nerolidol isomer mixture containing nerolidol isomers defined according to the structures:

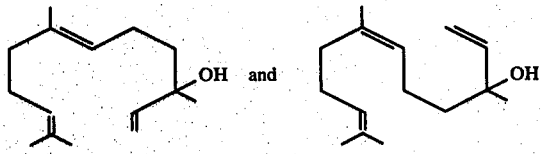

in the presence of a catalyst selected from the group consisting of potassium acid sulfate and paratoluene sulfonic acid at a temperature in the range of from 110° C. up to 200° C. and at a pressure in the range of from 1 mm/Hg pressure up to 200 atmospheres pressure, absolute.

2. The process of claim 1 wherein in the dehydrating process, the dehydration agent is potassium acid sulfate, the process is carried out in the presence of a hydrocarbon mineral oil solvent and the process is carried out at a temperature in the range of from 150° up to 200° at from 1 mm/Hg pressure up to 25 mm/Hg pressure.

3. The process of claim 1 wherein in the dehydrating process, the dehydrating agent is paratoluene sulfonic acid and the reaction temperature ranges from 115° C. at atmospheric pressure, at reflux, up to 200° C. at reflux and the reaction takes place in the presence of a solvent selected from the group consisting of toluene, xylene and a heavy hydrocarbon mineral oil.

* * * * *